US012778902B2

(12) United States Patent
Marquette et al.

(10) Patent No.: US 12,778,902 B2
(45) Date of Patent: Nov. 3, 2026

(54) FORMULATIONS COMPRISING A THERAPEUTIC PROTEIN AND AT LEAST ONE STABILIZER

(71) Applicant: UCB BIOPHARMA SRL, Brussels (BE)

(72) Inventors: Sarah Marquette, Brussels (BE); Christian Grandfils, Liège (BE); Jérôme Hurlet, Liège (BE)

(73) Assignee: UCB BIOPHARMA SRL, Brussels (BE)

( * ) Notice: Subject to any disclaimer, the term of this patent is extended or adjusted under 35 U.S.C. 154(b) by 415 days.

(21) Appl. No.: 18/282,554

(22) PCT Filed: Mar. 17, 2022

(86) PCT No.: PCT/EP2022/056977
§ 371 (c)(1),
(2) Date: Sep. 18, 2023

(87) PCT Pub. No.: WO2022/195008
PCT Pub. Date: Sep. 22, 2022

(65) Prior Publication Data

US 2025/0073179 A1 Mar. 6, 2025

(30) Foreign Application Priority Data

Mar. 18, 2021 (GB) ..................................... 2103785

(51) Int. Cl.

| | |
|---|---|
| ***A61K 9/70*** | (2006.01) |
| ***A61K 45/06*** | (2006.01) |
| ***A61K 47/10*** | (2017.01) |
| ***A61K 47/59*** | (2017.01) |
| ***B33Y 80/00*** | (2015.01) |

(52) U.S. Cl.
CPC ................ *A61K 9/70* (2013.01); *A61K 45/06* (2013.01); *A61K 47/10* (2013.01); *A61K 47/593* (2017.08); *B33Y 80/00* (2014.12)

(58) Field of Classification Search
CPC .......... A61K 9/70; A61K 45/06; A61K 47/10; A61K 47/593; A61K 9/0024; A61K 9/146; A61K 9/1641; A61K 9/1647; A61K 9/19; A61K 38/18; A61K 38/19; A61K 38/22; A61K 39/395; A61K 9/0092; A61K 39/39591; A61K 47/34; A61K 38/00; A61K 2039/505; B33Y 80/00
See application file for complete search history.

(56) References Cited

U.S. PATENT DOCUMENTS

| | | | |
|---|---|---|---|
| 4,526,938 | A | 7/1985 | Churchill et al. |
| 2010/0008998 | A1 | 1/2010 | Kang et al. |
| 2010/0316571 | A1 | 12/2010 | Simone et al. |
| 2014/0086974 | A1 | 3/2014 | Wu et al. |
| 2014/0205638 | A1 | 7/2014 | Oh et al. |
| 2015/0174300 | A1 | 6/2015 | Trollsas et al. |
| 2017/0106604 | A1 | 4/2017 | Dikovsky et al. |

FOREIGN PATENT DOCUMENTS

| | | |
|---|---|---|
| CN | 107 400 412 A | 11/2017 |
| CN | 110604747 | 12/2019 |
| JP | H 11513985 | 11/1999 |
| WO | WO 97/15287 | 5/1997 |
| WO | WO 99/18142 | 4/1999 |
| WO | WO 2017/134418 | 8/2017 |
| WO | WO 2017/137953 | 8/2017 |
| WO | WO 2019/195256 | 10/2019 |
| WO | WO2020/089249 | 5/2020 |
| WO | WO 2022/117512 | 6/2022 |

OTHER PUBLICATIONS

Stankovic et al. (Tailored protein release from biodegradable poly(e-caprolactone-PEG)-b-poly(e-caprolactone) multiblock-copolymer implants. European Journal of Pharmaceutics and Biopharmaceutics, 2014 (Year: 2014).*

Pereira et al. (Polymer Selection for HME Coupled to FDM in Pharmaceutics, pharmaceutics, 2020). (Year: 2020).*

Written Opinion in International Application No. PCT/EP2022/056977, Jul. 20, 2022, pp. 1-10.

Carlier, E. et al. "Development of mAb-loaded 3D-printed (FDM) implantable devices based on PLGA" *International Journal of Pharmaceutics*, available online Feb. 4, 2021, pp. 1-12, vol. 597, No. 120337.

Milacic, V. et al. "Lysozome release and polymer erosion behavior of injectable implants prepared from PLGA-PEG block copolymers and PLGA/PLGA-PEG blends" *Pharmaceutical Research*, Feb. 2014, pp. 1-24, vol. 31, No. 2.

Stanković, M. et al. "Tailored protein release from biodegradable poly(ϵ-caprolactone-PEG)-b-poly(ϵ-caprolactone) multiblock-copolymer implants" *European Journal of Pharmaceutics and Biopharmaceutics*, available online Mar. 3, 2014, pp. 329-337, vol. 87, No. 2.

(Continued)

*Primary Examiner* — Robert A Wax
*Assistant Examiner* — John Seungjai Kwon
(74) *Attorney, Agent, or Firm* — SALIWANCHIK, LLOYD & EISENSCHENK

(57) ABSTRACT

The invention relates to the field of pharmaceutical compositions comprising proteins as therapeutic active ingredient. More particularly it is directed to di-block or multi-block copolymers used as excipients, and in particular as stabilizer, in protein-containing dried compositions, filaments obtained from these dried compositions, implantable drug delivery device formed from these filaments and to methods of producing such compositions, filaments and devices.

20 Claims, 6 Drawing Sheets

(56) References Cited

OTHER PUBLICATIONS

Yin, J. et al. "Controlled release of FGF-2 and BMP-2 in tissue engineered periosteum promotes bone repair in rats" *Biomedical Materials*, published Jan. 9, 2018, pp. 1-10, vol. 13, No. 2.
Claims pending for U.S. Appl. No. 18/039,498, filed May 31, 2023, pp. 1-3.

* cited by examiner

A)

B)

A)

B)

A)

B)

FORMULATIONS COMPRISING A THERAPEUTIC PROTEIN AND AT LEAST ONE STABILIZER

CROSS-REFERENCE TO RELATED APPLICATION

This application is the U.S. national stage application of International Patent Application No. PCT/EP2022/056977, filed Mar. 17, 2022.

FIELD OF INVENTION

The invention relates to the field of pharmaceutical compositions comprising proteins as therapeutic active ingredient. More particularly it is directed to di-block or multi-block copolymers used as excipients, and in particular as stabilizer, in protein-containing dried compositions, filaments obtained from these dried compositions, implantable drug delivery device formed from these filaments and to methods of producing such compositions, filaments and devices.

BACKGROUND OF THE INVENTION

The hot melt extrusion (HME) is a technique already widely described and implemented in the pharmaceutical field to produce drug-loaded printable filaments (Goyanes et al., 2015). HME is based on the melting of polymeric material that is extruded through a die to obtain a homogeneous drug-loaded filament. HME is a free-solvent process which is easily scaled-up (Tiwari et al., 2016). However, this technique imposes relatively high temperatures for drug processing. Such temperatures may be usually reduced by adding a plasticizer, allowing the decrease of the glass transition temperature (Tg) of the polymer. Another alternative to decrease the temperature of extrusion could be the use of thermoplastic polymers characterized by a low molecular weight (Fredenberg et al., 2011). HME was already investigated to develop protein-based formulations which were characterized by a controlled-release of the loaded active ingredient over time (Cossé et al., 2016; Duque et al., 2018; Ghalanbor et al., 2010).

One of the major challenges remains the stabilization of the protein during the drying step before extrusion and then the extrusion step itself. Indeed, it was shown that the solid state of the protein could be more advantageous to promote a higher stability as well as to make easier its addition into the polymeric matrix using HME process (Cossé et al., 2016; Mensink et al., 2017). If several methods have been developed to dry protein that can then be extruded, spray-drying and freeze-drying being the most popular ones, their optimization remains today challenging and specific for each particular drug (Emami et al., 2018). During water elimination, the protein is submitted to several physico-chemical stresses, such as changes in pH or ionic strength, temperature gradient, interfacial interactions, change in hydration or shear stress. If drying optimisation can rely on processing parameters, such as temperature and flowrate of nebulization in case of spray-drying or freezing conditions and vacuum/temperature imposed for freeze-drying, stabilizers are typically used to protect the protein but also to facilitate water elimination. Most frequently these stabilizers are made from very low molecular weight hydrosoluble compounds, such as mono, disaccharide or oligosaccharides, inorganic or organic buffers and/or ionic or non-ionic surfactants. Hydrosoluble polymers are also generally added in order to provide cohesiveness to the resulting powders. All these compounds, typically added in high amounts relative to the biopharmaceutical drugs, i.e., up to at least 30 wt %, counteract their blending with hydrophobic degradable matrices. Indeed, being non-miscible with these polymers they induce phase separation with formation of a porous matrix. Consequently, all these inert ingredients significantly increase the risk of a rapid release of the biopharmaceutical actives (burst effect), especially when raising drug loading. Moreover, being water soluble those excipients do not enhance the final processing, either by plasticizing the blend, or/and by stabilizing interphases (solid or liquid or gas) typically generated during drug processing.

Therefore, there is still a need for further stabilisers that can be used to obtain powders, filaments and implantable drug delivery devices comprising therapeutic proteins, such as a cytokine, a growth factor, a hormone, an antibody or a fusion protein, wherein said therapeutic proteins are stable over time within these filaments and/or devices (e.g., limiting protein degradation during the production of the filament and then of the implantable drug delivery device).

SUMMARY OF THE INVENTION

In a first aspect, the present invention provides a pharmaceutical composition comprising at least one stabilizer, wherein said at least one stabilizer is a di-block or multi-block copolymer, an active ingredient, wherein said active ingredient is a therapeutic protein, and optionally a buffering agent, a surfactant and/or at least one further stabilizer. The di-block or multi-block copolymer, used as a stabilizer, is preferably formed from the combination of at least one PEG and at least one polymer selected from or based on polyurethane (TPU), polyvinylpyrrolidone (PVP), polyvinyl alcohol (PVA), poly(ε-caprolactone) (PCL), poly(lactic acid) (PLA), polydioxanone, polyglycolide, polytrimethylene carbonate, hydroxypropyl cellulose (HPC), Hydroxypropyl methylcellulose (HPMC), any variants thereof or combinations thereof. Examples of such di-block or multi-block copolymers are poly(lactide) poly(ethylene glycol) (PLA-PEG), poly(lactide) poly(ethylene glycol) poly(lactide) (PLA-PEG-PLA), poly(lactic-co-glycolic acid)-poly(ethylene glycol) (PLGA-PEG) poly[(lactide-co-ethylene glycol)-co-ethyloxyphosphate] (Poly(LAEG-EOP)), Polyvinyl caprolactam-polyvinyl acetate-polyethylene glycol (PCL-PVA-PEG).

In a second aspect, the present invention describes a filament for preparing an implantable drug delivery device, wherein the filament comprises at least one stabilizer and an active ingredient, wherein said at least one stabilizer is a di-block or multi-block copolymer and wherein said active ingredient is a therapeutic protein. Preferably, the di-block or multi-block copolymer is formed from the combination of at least one PEG and at least one polymer selected from or based on polyurethane (TPU), polyvinylpyrrolidone (PVP), polyvinyl alcohol (PVA), poly(¿-caprolactone) (PCL), poly(lactic acid) (PLA), polydioxanone, polyglycolide, polytrimethylene carbonate, hydroxypropyl cellulose (HPC), Hydroxypropyl methylcellulose (HPMC), any variants thereof or combinations thereof. Examples of such di-block or multi-block copolymers are poly(lactide) poly(ethylene glycol) (PLA-PEG), poly(lactide) poly(ethylene glycol) poly(lactide) (PLA-PEG-PLA), poly(lactic-co-glycolic acid)-poly(ethylene glycol) (PLGA-PEG) poly[(lactide-co-ethylene glycol)-co-ethyloxyphosphate] (Poly(LAEG-EOP)), Polyvinyl caprolactam-polyvinyl acetate-polyethylene glycol (PCL-PVA-PEG).

In a third aspect, the present invention relates to a filament which further comprises a polymeric material, and a plasticizer. The filament may further comprise a buffering agent and/or a surfactant.

In a fourth aspect, the present invention describes an implantable drug delivery device formed out of, comprising or consisting of one or more layers made from a filament comprising at least one stabilizer and an active ingredient, wherein said stabilizer is a di-block or multi-block copolymer and wherein said active ingredient is a therapeutic protein. The implantable drug delivery device further comprises a polymeric material, and a plasticizer. It may also comprise a buffering agent and/or a surfactant.

In a fifth aspect, the present invention provides a process for producing a filament for preparing an implantable drug delivery device, the process comprising the steps of:

a. preparing a liquid formulation comprising or consisting of the active ingredient, at least one stabilizer and optionally a buffering agent and/or a surfactant,
b. freeze-drying or spray-drying the liquid formulation of step a to obtain a powder,
c. dispersing homogeneously the powder of step b. with a plasticizer and at least one polymeric material,
d. spinning or extruding the dispersion of step c. to obtain a filament.

In a sixth aspect, the present invention relates to a process for producing an implantable drug delivery device, the process comprising:

a. loading of the filament herein described into the print head of the 3D printer using a temperature above the glass transition temperature,
b. heating of the build platform at a temperature below the glass transition temperature of the polymeric matrix,
c. depositing said heated filament through a nozzle to build the device from at least the first layer to the final top layer.

Definitions

The term “powder” (powders in its plural form) refers to a dry “particle” of very small size (size typically of about 20 μm or below) (alternatively named “microparticles” or “microspheres”). Preferably the powder contains water below about 10%, usually below 5% or even below 3% by weight of the dry particles. A powder can typically be obtained by spray-drying and/or freeze-drying an aqueous solution or an aqueous emulsion. Alternatively, the term dry powder can be used.

The term “freeze-drying” also known as “lyophilization” refers to a process for obtaining a powder comprising at least three main steps: 1) lowering the temperature of the product to be freeze-dried to below freezing point (typically between −40 and −80° C.; freezing step), 2) high-pressure vacuum (typically between 30 and 300 mTorr; first drying step) and 3) increasing the temperature (typically between 2° and 40° C.; second drying step).

The term “spray drying” refers to a process for obtaining powders comprising at least two main steps: 1) atomizing a liquid feed into fine droplets and 2) evaporating the solvent or water by means of a hot drying gas.

The term “stability”, as used herein, refers to the physical, chemical, and conformational stability of the active ingredient (herein a therapeutic protein) in the filaments and drug delivery devices according to the present invention (and including maintenance of biological potency). Instability of the proteins may be caused by chemical degradation or aggregation of the proteins to form for instance higher order polymers, deglycosylation, modification of glycosylation, oxidation or any other structural modification that reduces the biological activity of the formulated protein. The term “stable” refers to filaments or drug delivery devices in which the active ingredient (herein a therapeutic protein) essentially retains its physical, chemical and/or biological properties during manufacturing and upon storage. In order to measure the protein stability in a formulation, various analytical methods are well within the knowledge of the skilled person (see some examples in the example section). Various parameters can be measured to determine stability (in comparison with the initial data), such as (and not limited to): 1) no more than about 15% of alteration of the monomeric form of the antibody, or 2) no more than 15% High Molecular Weight Species (HMW or HMWS; also herein referred to as aggregates).

The term “buffer” or “buffering agent”, as used herein, refers to solutions of compounds that are known to be safe in formulations for pharmaceutical use and that have the effect of maintaining or controlling the pH of the formulation in the pH range desired for said formulation. Acceptable buffers for controlling pH at a moderately acidic pH to a moderately basic pH include, but are not limited to, phosphate, acetate, citrate, arginine, TRIS (2-amino-2-hydroxymethyl-1,3,-propanediol), histidine buffers and any pharmacologically acceptable salt thereof.

The term “surfactant”, as used herein, refers to a soluble compound which can affect interfacial tension between different phases could be either liquid, solid or gas phases. Accordingly, surfactant can be used notably to increase the water solubility of hydrophobic, oily substances or otherwise increase the miscibility of two substances with different hydrophobicity. Surfactants are commonly used in formulations, notably in order to modify the absorption of the drug or its delivery to the target tissues. Well known surfactants include polysorbates (polyoxyethylene derivatives; Tween) as well as poloxamers (i.e., copolymers based on ethylene oxide and propylene oxide, also known as Pluronics®).

The term “stabilizing agent” or “stabilizer”, as used herein, is a compound that is physiologically tolerated and imparts a suitable stability/tonicity to a formulation. During freeze-drying (lyophilization) process or spray drying process, the stabilizer is also effective as a protectant. Compounds such as glycerine, are commonly used for such purposes. Other suitable stabilizing agents include, but are not limited to, amino acids or proteins (e.g., glycine or albumin), salts (e.g., sodium chloride), and sugars (e.g., dextrose, mannitol, sucrose, trehalose and lactose), as well as those described in the frame of the present disclosure.

The term “polymeric material” refers to polymeric components able to flow and to support high temperatures during hot melt extrusion (HME) and 3D printing for instance. Therefore, the preferred polymeric materials according to the invention are thermoplastic polymers or thermoresistant polymers. Examples of such thermoplastic polymers that are commonly used for 3D printing are for instance are Polyvinylpyrrolidone (PVP), acrylonitrile butadiene styrene (ABS), the poly(lactic acid) (PLA) (either as PLLA or PDLA, as both forms can be used indifferently), Poly(lactic-co-glycolic acid) (PLGA), the polyvinyl alcohol (PVA), poly(ε-caprolactone) (PCL), ethylene vinyl acetate (EVA). Preferably they are biodegradable or bioeliminable for more convenience to the patients. Other thermoresistant polymeric material are for instance hydroxypropyl cellulose (HPC), Hydroxypropyl methylcellulose (HPMC), Poly(Ethylene Glycol) (PEG), Eudragit derivatives (E, RS, RL, EPO), Polyvinyl caprolactam-polyvinyl acetate-polyethylene glycol graft co-polymer (Soluplus®), thermoplastic polyurethane (TPU). Suitable polymeric materials are also herein described.

The term "PEG" refers to Poly(Ethylene Glycol). Alternatively, the acronym PEO (standing for Poly(Ethylene Oxyde) can be used. Although PEG tends to be used for polymers up to 20 kDa and PEO for larger polymers, both names/acronyms can be used indifferently whatever the size of the polymer.

The term "plasticizer" refers to a compound that can be combined with a thermoplastic polymer for instance in order to increase its plasticity or to decrease its viscosity. It can also help to decrease the glass transition temperature (Tg) of said polymer. Examples of such plasticizers that can be used in the pharmaceutic industry are for instance bio-based plasticizers such as Alkyl citrates (e.g., Acetyl triethyl citrate (ATEC), Triethyl citrate (TEC)), triacetin (TA), Methyl ricinoleate, Epoxidized vegetable oils or yet Poly Ethylene Glycol (PEG) (depending on its molecular weight, PEG can act either as polymeric matrix or as a plasticizer), castor oil, Vitamin E TPGS (D-α-tocopheryl polyethylene glycol 1000 succinate), Fatty acid esters (butyl stearate, glycerol monostearate, stearyl alcohol), pressurized carbon dioxide, surfactant (polysorbate 80) (see, e.g., Crowley 2007) Suitable plasticizers are also herein described.

The term "protein" or "therapeutic protein" refers to protein is a cytokine, a growth factor, a hormone, an antibody or a fusion protein, for therapeutic use. Preferably the protein is a recombinant protein, produced by recombinant method.

The term "antibody" as used herein includes, but is not limited to, monoclonal antibodies, polyclonal antibodies and recombinant antibodies that are generated by recombinant technologies as known in the art. "Antibody" include antibodies of any species, in particular of mammalian species; such as human antibodies of any isotype, including IgG1, IgG2a, IgG2b, IgG3, IgG4, IgE, IgD and antibodies that are produced as dimers of this basic structure including IgGA1, IgGA2, or pentamers such as IgM and modified variants thereof; non-human primate antibodies, e.g., from chimpanzee, baboon, rhesus or cynomolgus monkey; rodent antibodies, e.g., from mouse, or rat; rabbit, goat or horse antibodies; camelid antibodies (e.g., from camels or llamas such as Nanobodies™) and derivatives thereof; antibodies of bird species such as chicken antibodies; or antibodies of fish species such as shark antibodies. The term "antibody" also refers to "chimeric" antibodies in which a first portion of at least one heavy and/or light chain antibody sequence is from a first species and a second portion of the heavy and/or light chain antibody sequence is from a second species. Chimeric antibodies of interest herein include "primatized" antibodies comprising variable domain antigen-binding sequences derived from a non-human primate (e.g., Old World Monkey, such as baboon, rhesus or cynomolgus monkey) and human constant region sequences. "Humanized" antibodies are chimeric antibodies that contain a sequence derived from non-human antibodies. For the most part, humanized antibodies are human antibodies (recipient antibody) in which residues from a hypervariable region of the recipient are replaced by residues from a hypervariable region [or complementarity determining region (CDR)] of a non-human species (donor antibody) such as mouse, rat, rabbit, chicken or non-human primate, having the desired specificity, affinity, and activity. In most instances residues of the human (recipient) antibody outside of the CDR; i.e., in the framework region (FR), are additionally replaced by corresponding non-human residues. Furthermore, humanized antibodies may comprise residues that are not found in the recipient antibody or in the donor antibody. These modifications are made to further refine antibody properties. Humanization reduces the immunogenicity of non-human antibodies in humans, thus facilitating the application of antibodies to the treatment of human disease. Humanized antibodies and several different technologies to generate them are well known in the art. The term "antibody" also refers to human antibodies, which can be generated as an alternative to humanization. For example, it is possible to produce transgenic animals (e.g., mice) that are capable, upon immunization, of producing a full repertoire of human antibodies in the absence of production of endogenous murine antibodies. Other methods for obtaining human antibodies/antibody fragments in vitro are based on display technologies such as phage display or ribosome display technology, wherein recombinant DNA libraries are used that are either generated at least in part artificially or from immunoglobulin variable (V) domain gene repertoires of donors. Phage and ribosome display technologies for generating human antibodies are well known in the art. Human antibodies may also be generated from isolated human B cells that are ex vivo immunized with an antigen of interest and subsequently fused to generate hybridomas which can then be screened for the optimal human antibody. The term "antibody" refers to both glycosylated and aglycosylated antibodies. Furthermore, the term "antibody" as used herein not only refers to full-length antibodies, but also refers to antibody fragments, more particularly to antigen-binding fragments thereof. A fragment of an antibody comprises at least one heavy or light chain immunoglobulin domain as known in the art and binds to one or more antigen(s). Examples of antibody fragments according to the invention include a Fab, modified Fab, Fab', modified Fab', F(ab')2, Fv, Fab-Fv, Fab-dsFv, Fab-Fv-Fv, scFv and Bis-scFv fragment. Said fragment can also be a diabody, tribody, triabody, tetrabody, minibody, single domain antibody (dAb) such as sdAb, VL, VH, VHH or camelid antibody (e.g., from camels or llamas such as a Nanobody™) and VNAR fragment. An antigen-binding fragment according to the invention can also comprise a Fab linked to one or two scFvs or dsscFvs, each scFv or dsscFv binding the same or a different target (e.g., one scFv or dsscFv binding a therapeutic target and one scFv or dsscFv that increases half-life by binding, for instance, albumin). Exemplary of such antibody fragments are FabdsscFv (also referred to as BYbeR) or Fab-(dsscFv) 2 (also referred to as TrYbe®, see WO2015/197772 for instance). Antibody fragments as defined above are known in the art.

Unless otherwise specified, a value percent (%) refers to percent by weight (alternatively named wt % of % w/w or % weight/weight.

The terms "Low molecular weight", "Low Mw" or "LMW" are used herein to refer to molecules having a weight at or below 20 kDa. Copolymers having a low molecular weight copolymers should preferably be dissolvable in aqueous medium to give rise to true solutions or to micellar solutions. To the contrary, the terms "High molecular weight", "High Mw" or "HMW" are used herein to refer to molecules having a weight above 20 kDa.

DETAILED DESCRIPTION OF THE INVENTION

Based on the advantages of Hot Melt Extrusion technologies (HME), the inventors have developed mAb-loaded filaments. They have used these filaments to obtain implantable devices, such as via 3D-printing of implantable devices using Fused Deposition Modelling (FDM) technology. The present invention is based on the surprising finding that it has been possible, by combining proteins (such as antibodies) with low molecular weight di-block or multi-block copolymers, not only to produce a filament comprising a protein but also having a high protein load (at 15% and higher) and to use said filament in an implantable drug delivery device. It was also shown that the protein was stable over time (limited aggregation/degradation) under a freeze-dried/spray-dried state (e.g., as a powder), in filaments or in implantable drug delivery systems. It was necessary to judiciously select the type of di-block or multi-block copolymers to be used to obtain powders and filaments that were then usable, for instance, in an implantable drug delivery device.

More specifically, it is a finding of the inventors that low molecular weight di-block or multi-block copolymers, made for instance of PEG-PLA or PEG-PLGA, can stabilise therapeutic proteins (such as antibodies), during their processing and storage, more specifically in a dry state. Thanks to their composition, macromolecular architecture and molecular weight, these copolymers play at least the three following roles during biopharmaceutical drying. Being made from PEG, they act as water replacement. Adjusting properly their hydrophilic to lipophilic balance, acting on the respective lengths of the polyether to polyester segments respectively, their amphiphilic features could be precisely adjusted. Thanks to the amorphous behaviour and macromolecular features they provide bulking and cohesiveness to the final solid. Being made from a polyester sequence, these di-block or multi-block copolymers also promote the intimate mixing of protein drugs within the hydrophobic aliphatic polyester. Last but not least, when the processing technology relies on HME to blend the protein drug within the thermoplastic polymer, the PEG sequence of the di-block or multi-block copolymer could also act as plasticizer to reduce the temperature of processing, a critical aspect to avoid thermal degradation of biopharmaceutical drug.

The main object of the present invention is a di-block or multi-block copolymer for use as a stabilizer in pharmaceutical compositions, whereas the pharmaceutical compositions preferably comprise a therapeutic protein as an active ingredient, and wherein said di-block or multi-block copolymer is formed or obtained from the combination of at least one PEG and at least one polymer selected from or based on polyurethane (TPU), polyvinylpyrrolidone (PVP), polyvinyl alcohol (PVA), poly(ε-caprolactone) (PCL), poly(lactic acid) (PLA) (either as PDLA or PLLA), polydioxanone, polyglycolide, polytrimethylene carbonate, hydroxypropyl cellulose (HPC), Hydroxypropyl methylcellulose (HPMC), any variants thereof and/or combinations thereof. Examples of such di-block or multi-block copolymers are poly(lactide) poly(ethylene glycol) (PLA-PEG), poly(lactide) poly(ethylene glycol) (PLGA), poly (lactide) poly(ethylene glycol) poly(lactide) (PLA-PEG-PLA), poly(lactic-co-glycolic acid)-poly(ethylene glycol) (PLGA-PEG) poly[(lactide-co-ethylene glycol)-co-ethyloxyphosphate] (Poly(LAEG-EOP)), Polyvinyl caprolactam-polyvinyl acetate-polyethylene glycol (PCL-PVA-PEG). These copolymers can have different ratios of PEG:polymer, such as but not limited to 5:1 to 1:1. The copolymers have preferably a total size of about 200 Da to about 15 kDa, even preferably 400 Da to about 12 kDa, or even preferably 5 kDa to about 10 kDa, such as 5.0, 5.5, 6.0, 6.5, 7.0, 7.5, 8.0, 8.5, 9.0, 9.5 or 10 kDa. Although copolymers of up to 15 kDa can be successfully used in the context of the invention, copolymers having a size at or below 12 kDa, or at or below 10 kDa further enhance the miscibility with the polymeric material, but also facilitate their dispersion and interaction with the active agent. Such copolymers are preferably present before being dried in an ratio (weight/weight or w/w) therapeutic protein: copolymers of 100:1 to 6:1 (w/w), preferably in an amount of 20:1 to 10:1 (w/w), such as 20:1, 19:1, 18:1, 17:1, 16:1, 15:1, 14:1, 13:1, 12:1, 11:1 or 10:1. The skilled person will know how to adapt the ratios in order to enhance their solubility, or at least their dispersability, in aqueous medium in order to promote their interaction with the biopharmaceutical active ingredient. Said stabilizer is particularly useful for stabilizing therapeutic proteins (such as antibodies), during their processing (starting from example from a liquid pharmaceutical composition) and storage, more specifically in a dry state.

Based on the properties of the di-block or multi-block copolymer identified by the inventors, herein provided is also a di-block or multi-block copolymer as herein described for use as an excipient for the drying, such as via freeze-drying or spray-draying technics, of liquid pharmaceutical compositions comprising an active ingredient, and optionally a buffering agent, at least one further stabilizer and/or a surfactant, wherein said active ingredient is a therapeutic protein.

Also encompassed by the present invention is a pharmaceutical composition comprising at least one stabilizer and an active ingredient, wherein said at least one stabilizer is a di-block or multi-block copolymer as herein described and wherein said active ingredient is a therapeutic protein. Said pharmaceutical composition optionally comprises a buffering agent, a surfactant and/or at least one further stabilizer. Said pharmaceutical composition, when in the liquid state, can then be dried, for instance via freeze-drying or spray-drying technics. Once dried, it can be utilised as such or alternatively can be further processed in filaments for instance via hot melting extrusion or spinning.

Another object of the present invention is a filament for preparing an implantable drug delivery device, wherein the filament comprises at least one stabilizer and an active ingredient, wherein said at least one stabilizer is a di-block or multi-block copolymer as herein described, and wherein said active ingredient is a therapeutic protein. Said filament further comprises polymeric material, and a plasticizer. Said filament may further comprise at least one additional excipient, such as a buffering agent, a surfactant and/or at least one further stabilizer. The filament can then be moulded or used in a 3D printer in order to obtain an implantable drug delivery device of any desired shape. Alternatively, an object of the present invention is a filament for preparing an implantable drug delivery device, wherein the filament comprises at least one di-block or multi-block copolymer as herein described and an active ingredient, wherein said active ingredient is a therapeutic protein. Said filament further comprises a polymeric material, and a plasticizer. Said filament may further comprise at least one additional excipient, such as a buffering agent, a surfactant and/or at least one further stabilizer. Filament can be used as such or can then be moulded or used in a 3D printer in order to obtain an implantable drug delivery device of any desired shape.

The invention further provides an implantable drug delivery device formed out of, comprising or consisting of one or more layers made from a filament comprising at least one stabilizer and an active ingredient, wherein said at least one stabilizer is a di-block or multi-block copolymer as herein described and wherein said active ingredient is a therapeutic protein. The filament further comprises a polymeric material, and a plasticizer. Said filament may further comprise at least one additional excipient, such as a buffering agent, a surfactant and/or at least one further stabilizer. Alternatively, herein provided is an implantable drug delivery device formed out of, comprising or consisting of one or more layers made from a filament comprising at least one di-block or multi-block copolymer as herein described and an active ingredient, wherein said active ingredient is a therapeutic protein. The filament further comprises a polymeric material, and a plasticizer. Said filament may further comprise at least one additional excipient, such as a buffering agent, a surfactant and/or at least one further stabilizer.

Before being added to the polymeric material to form the filament and then the implantable drug delivery device, the active ingredient and the at least one stabilizer (typically in a previous liquid state) have to be spray-dried or freeze-dried. To do so, a preliminary liquid pharmaceutical composition is prepared wherein said pharmaceutical composition comprises or consists of the active ingredient, at least one stabilizer and optionally a buffering agent and/or a surfactant, wherein said at least one stabilizer is a di-block or multi-block copolymer as herein described. Said liquid pharmaceutical composition is then spray-dried or freeze-dried according to standard methods to obtain powders. Once in the form of powders (i.e., dried microparticles), the active ingredient is homogeneously dispersed into the at least one polymeric matrix and the plasticizer. They form an active ingredient-loaded solid dispersion such as a therapeutic protein-loaded solid dispersion.

Therefore, herein also provided is a process for producing the filament according to the invention, the process comprising the steps of:

a. preparing a liquid pharmaceutical composition comprising or consisting of the active ingredient, wherein said active ingredient is a therapeutic protein, at least one stabilizer, wherein said at least one stabilizer is a di-block or multi-block copolymer as herein described, and optionally a buffering agent, a surfactant and/or at least one further stabilizer,
b. freeze-drying or spray-drying the liquid pharmaceutical composition of step a. to obtain a powder,
c. dispersing homogeneously the powder of step b. with a plasticizer and at least one polymeric material, (also named herein active ingredient-loaded solid dispersion),
d. spinning or extruding the dispersion of step c. to obtain a filament.

Before step a., the at least one stabilizer can be solubilized in water or in a buffer of choice before being added to the other components of the liquid formulation. Alternatively, the at least one stabilizer can be solubilized directly with the other components of the liquid pharmaceutical composition.

For step d., different techniques of spinning or extrusion can be used such as (but not limited to) wet spinning, melt spinning, gel spinning, emulsion spinning or yet hot melt extrusion (HME).

The filament according to this invention can be used for producing an implantable drug delivery device. Said device can be either cut to a desired length, pelletized, moulded, grinded, or 3D printed. The advantage of using a 3D printer is to enable the design and manufacture of novel and customized implantable drug delivery device that are not possible using traditional processes. Thanks to 3DP technology, the structure, shape or composition of the device can be customized and adapted to the patient on a case by case basis. Another advantage of using a 3D printer is to provide devices on demand.

3D printing is part of a technology called additive layer manufacturing (ALM). ALM can be based on liquid solidification or on solid material extrusion. Liquid solidification technologies include for instance Drop-on-powder deposition (DoP, or binder jetting), drop-on-drop deposition (DOD), whereas solid material extrusion technologies includes Pressure-assisted microsyringe (PAM) deposition, or yet Fused Filament Fabrication (FFF), also known as Fused Deposition Modeling™ (FDM®) technology. In a DoP or DoD system, two-dimensional layers are repeatedly printed until a three-dimensional object is formed. For example, inkjet or polyjet printing of dosage forms as disclosed herein can use additive manufacturing. The PAM technology involves the deposition of soft material (semi-solid or viscous) through a syringe-based print head. The syringe is typically loaded with the material which is then extruded using pneumatic pressure, plunger or a screw. The FDM technology is based on the extrusion of thermoplastic polymer which is driven by a gear system through a heated nozzle tip. The print head is composed of the pinch roller mechanism, a liquefier block, a nozzle and a gantry system that manages the x-y directions. The filament is fed and melt in the liquefier, turning the solid into a softened state. The solid part of the filament is used as a plunger to push the melt through the nozzle tip (Sadia et al., 2016). Once a layer of thermoplastic melt is deposited, the build platform is lowered, and the process is repeated to build the structure in a layer-wise manner.

Also encompassed by the invention is a process for producing an implantable drug delivery device according to the invention as a whole, and in particular a 3D printed implantable drug delivery device, the process comprising the steps of:

a. loading of the filament into the print head of the 3D printer using a temperature above the glass transition temperature,
b. heating of the build platform at a temperature below the glass transition temperature of the polymeric matrix,
c. depositing said heated filament through a nozzle to build the device from at least the first layer to the final top layer.

The at least one stabilizer according to the present invention as a whole is a di-block copolymer or a multi-block copolymer (also encompassing graft-copolymers, dentrimer copolymers or star copolymers) formed (or obtained) from the combination of at least one PEG (polyethylene glycol) and at least one hydrophobic polymer selected from or based on polyurethane (TPU), polyvinylpyrrolidone (PVP), polyvinyl alcohol (PVA), poly(ε-caprolactone) (PCL), poly(lactic acid) (PLA) (either as PLLA or PDLA), polydioxanone, polyglycolide, polytrimethylene carbonate, hydroxypropyl cellulose (HPC), Hydroxypropyl methylcellulose (HPMC), any variants thereof or physical or chemical combinations thereof. Examples of such di-block or multi-block copolymers are poly(lactide) poly(ethylene glycol) (PLA-PEG), poly(lactide) poly(ethylene glycol) poly(lactide) (PLA-PEG-PLA), poly(lactic-co-glycolic acid)-poly(ethylene glycol) (PLGA-PEG) poly[(lactide-co-ethylene glycol)-co-ethyloxyphosphate] (Poly(LAEG-EOP)), Polyvinyl caprolactam-polyvinyl acetate-polyethylene glycol (PCL-PVA-PEG). These copolymers can have different ratios of PEG:polymer, such as but not limited to 5:1 to 1:1. The copolymers have preferably a total size of about 200 Da to about 15 kDa, even preferably 400 Da to about 12 KDa, or even preferably 5 kDa to about 10 Kda, such as 5.0, 5.5, 6.0, 6.5, 7.0, 7.5, 8.0, 8.5, 9.0, 9.5 or 10 kDa. Although copolymers of up to 15 kDa can be successfully used in the context of the invention, copolymer having a size at or below 12 kDa or at or below 10 kDa further enhance their miscibility with the polymeric material, but also to facilitate their dispersion and interaction with the active agent. Should such copolymers be used as an at least one stabilizer, they will be present before being dried in an ratio (weight/weight or w/w) therapeutic protein:stabilizer of 100:1 to 6:1 (w/w), preferably in an amount of 20:1 to 10:1 (w/w), such as 20:1, 19:1, 18:1, 17:1, 16:1, 15:1, 14:1, 13:1, 12:1, 11:1 or 10:1. The skilled person will know how to adapt the ratios in order to enhance their solubility, or at least their dispersibility, in aqueous medium in order to promote their interaction with the biopharmaceutical active.

Should more than one stabilizer be used, the at least one further stabilizer according to the present invention as a whole is preferably added before the drying step (i.e., before freeze-drying or spray-drying). When present, said at least one further stabilizer is preferably a disaccharide (such as sucrose or trehalose), a cyclic oligosaccharide (such as hydroxypropyl-β-cyclodextrine), a polysaccharide (such as inulin), a polyol (such as sorbitol), or an amino acid (such as L-Arginine, L-Leucine, L-phenylalanine or L-Proline) or combination thereof. The combinations of stabilizers can be for instance (without any limitation) one copolymer as described above with at least a disaccharide, an amino acid, a polyol, or any combination thereof (such as one copolymer as described above combined with one disaccharide and one amino acid or combined with a polyol and an amino acid).

Before being dried, the at least one stabilizer is preferably present in the preliminary liquid formulation at a concentration of or of about 10 mg/mL to or to about 100 mg/mL, preferably of or of about 20 mg/mL to or to about 75 mg/mL, or preferably of or of about 30 mg/mL to or to about 70 mg/mL or even preferably of or of about 35 mg/mL to or to about 65 mg/mL such as 35, 36, 37, 38, 39, 40, 41, 42, 43, 44, 45, 46, 47, 48, 49, 50, 51, 52, 53, 54, 55, 56, 57, 58, 59, 60, 61, 62, 63, 64 or 65 mg/mL. Alternatively, before being dried, the stabilizer is present in the preliminary liquid formulation at a concentration of or of about 1 to or to about 10% w/v (weight/volume), or preferably at a concentration of or of about 2 to or to about 7.5% w/v, or preferably of or of about 3 to or to about 7% or even preferably of or of about 3.5 to or to about 6.5% such as 3. 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4 or 6.5% w/v.

In the context of the invention as a whole, the active ingredient is a therapeutic protein. Said therapeutic protein can be any a therapeutic protein as defined in the definition section. Before being dried, the therapeutic protein is preferably present in the preliminary liquid formulation at a concentration of or of about 50 mg/mL to or to about 300 mg/mL, preferably of or of about 65 mg/mL to or to about 250 mg/mL, even preferably of or of about 80 mg/mL to or to about 200 mg/ml such as 80, 85, 90, 95, 100, 105, 110, 115, 120, 125, 130, 135, 140, 145, 150, 155, 160, 165, 170, 175, 180, 185, 190, 195 or 200 mg/mL. Alternatively, before being dried, the therapeutic protein is present in the preliminary liquid formulation at a concentration of or of about 5 to or to about 30% w/v (weight/volume), or preferably at a concentration of or of about 6.5 to or to about 25% w/v, even preferably of or of about 8 to about 20% such as 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 or 20% w/v. The therapeutic protein loading in the filament, and thus in the final implantable drug delivery device, is preferably in an amount of about 5 to 40% (weight/weight or w/w), or in an amount of about 10 to 35% (w/w), or yet of about 15 to 35% (w/w) such as 15, 16, 17, 18, 19, 20, 21, 22, 23, 24, 25, 26, 27, 28, 29, 30, 31, 32, 33, 34 or 35% (w/w).

According to the present invention in its entirety, should a buffering agent be present, said buffering agent can be selected from the group comprising or consisting of (but not limited to) phosphate, acetate, citrate, arginine, trisaminomethane (TRIS), and histidine. Before being dried, said buffering agent is preferably present in the preliminary liquid formulation in an amount of from about 5 mM to about 100 mM of the buffering agent, and even preferably from about 10 mM to about 50 mM, such as about 10, 15, 20, 25, 30, 35, 40, 45 or 50 mM.

In the context of the whole disclosure, a surfactant may be present. Said surfactant can be for instance (but without being limited to) Polysorbate 20 (PS20) or Polysorbate 80 (PS80). When present, the surfactant is preferably added in the preliminary liquid formulation, i.e., before the drying step. Said surfactant is preferably present in the preliminary liquid formulation present in the formulations in an amount of or of about 0.01 to or to about 5 mg/mL, more preferably of or of about 0.01 to or to about 1 mg/mL, more particularly of or of about 0.1 to or to about 0.6 mg/mL, such as 0.1, 0.15, 0.2, 0.25, 0.3, 0.35, 0.4, 0.45, 0.5, 0.55 or 0.6 mg/mL. Alternatively, the polysorbate surfactant is preferably present in the preliminary liquid formulation in an amount expressed in term of % weight per 100 mL (% w/v). In such as case, the polysorbate surfactant comprised in the formulations according to the present invention as a whole can be present in an amount of 0.001 to 0.5% w/v, preferably from 0.01 to 0.1% w/v, or even preferably from 0.01 to 0.06% w/v such as 0.01, 0.015, 0.02, 0.025, 0.03, 0.035, 0.04, 0.045, 0.05, 0.055 or 0.06% w/V.

In the context of the present invention, and in particular when referring to filaments or final implantable drug delivery devices, the optional buffering agent, the optional surfactant and any further optional excipients (including any further stabilizers) are regrouped under the collective name of excipients. The excipients are preferably present in the filament, and thus in the final implantable drug delivery device, in a total amount of or of about 3 to or to about 20% w/w, preferably in a total amount of or of about 5 to 15% w/w, such as about 5, 5.5, 6, 6.5, 7, 7.5, 8, 8.5, 9, 9.5, 10, 10.5, 11, 11.5, 12, 12.5, 13, 13.5, 14, 14.5 or 15 wt %.

In the context of the invention as a whole, the at least one polymeric material is preferably a biodegradable, and biocompatible and/or bioeliminable thermoplastic polymer such as polyurethane (TPU), polyvinylpyrrolidone (PVP), polyvinyl alcohol (PVA), poly(¿-caprolactone) (PCL), poly (lactic acid) (PLA) (either as PLLA or PDLA), polydioxanone, polyglycolide, polytrimethylene carbonate, hydroxypropyl cellulose (HPC), Hydroxypropyl methylcellulose (HPMC) or combinations thereof such as, but not limited to, ethylene vinyl acetate (EVA), poly(lactic-co-glycolic acid) (PLGA), poly(L-lactide-co-caprolactone-co-glycolide) (PLGA-PCL). Polymeric materials can have a controlled size of about 200 Da to about 50 kDa, preferably about 500 Da to about 40 kDa even preferably about 1 kDa to about 20 kDa, such as about 1, 2, 5, 10, 15 or 20 kDa. Alternatively, instead of having a given size (±), the polymeric materials can be a mix of polymers of different sizes, e.g., 5 kDa to 20 kDa or 7 kDa to 17 kDa. For instance, some commercially available polymers are a mix of polymers of different sizes such as Resomer® RG502 having a mix of polymers ranged between 7 and 17 kDa). Preferably said polymeric material is present in the filament, and thus in the final implantable drug delivery device, in an amount of about 50 to 75% (w/w), or in an amount of about 55 to 70% (w/w), such as 55, 56, 57, 58, 59, 60, 61, 62, 63, 64, 65, 66, 67, 68, 69 or 70%.

In the context of the invention as a whole, the plasticizer is preferably polyethylene glycol (PEG) or a PEG compound such as, but not limited to, maleimido monomethoxy PEG, activated PEG polypropylene glycol, methoxypoly(ethyleneglycol) polymer. PEG compounds according to the invention can also be charged or neutral polymers of the following types: dextran, colominic acids, or other carbohydrate-based polymers, polymers of amino acids, and biotin and other affinity reagent derivatives. PEG or PEG compounds in the context of the invention can be linear or branched. PEG or PEG compounds in the context of the invention can have a size of about 200 Da to about 50 kDa, preferably about 500 Da to about 40 kDa even preferably about 1 kDa to about 20 kDa, such as about 1, 2, 5, 10, 15 or 20 kDa. Alternatively, the plasticizer can be a di-block copolymer or multi-block copolymer described above as stabilizer as they contain enough PEG moiety to act as well as a plasticizer. Therefore, the plasticizer can be a di-block copolymer or a multi-block copolymer (also encompassing graft-copolymers, dentrimer copolymers or star copolymers) formed from the combination of at least one PEG (polyethylene glycol) and at least one hydrophobic polymer selected form or based on polyurethane (TPU), polyvinylpyrrolidone (PVP), polyvinyl alcohol (PVA), poly(s-caprolactone) (PCL), poly(lactic acid) (PLA) (either as PLLA or PDLA), polydioxanone, polyglycolide, polytrimethylene carbonate, hydroxypropyl cellulose (HPC), Hydroxypropyl methylcellulose (HPMC), any variants thereof or physical or chemical combinations thereof. Examples of such di-block or multi-block copolymers are poly(lactide) poly(ethylene glycol) (PLA-PEG), poly(lactide) poly(ethylene glycol) poly(lactide) (PLA-PEG-PLA), poly(lactic-co-glycolic acid)-poly (ethylene glycol) (PLGA-PEG) poly[(lactide-co-ethylene glycol)-co-ethyloxyphosphate] (Poly(LAEG-EOP)), Polyvinyl caprolactam-polyvinyl acetate-polyethylene glycol (PCL-PVA-PEG). These copolymers can have different ratios of PEG:polymer, such as but not limited to 5:1 to 1:1. The copolymers have preferably a total size of about 200 Da to about 15 kDa, even preferably 400 Da to about 12 KDa, or even preferably 5 kDa to about 10 KDa, such as 5.0, 5.5, 6.0, 6.5, 7.0, 7.5, 8.0, 8.5, 9.0, 9.5 or 10 kDa. Preferably said plasticizer is present in the filament, and thus in the final implantable drug delivery device, in an amount of about 2-20% (w/w), or preferably in an amount of about 5 to 15% (w/w), such as 5, 6, 7, 8, 9, 10, 11, 12, 13, 14 or 15% (w/w).

In the context of the invention as a whole, the plasticizer and the at least one polymeric material can be replaced in all or in part by a di-block copolymer or multi-block copolymer as herein described. That means that di-block copolymers or multi-block copolymers as herein described can be used either as stabilizer before freeze-drying or spray-drying or both as a stabilizer and plasticizer/polymeric material for spinning or extrusion via HME for instance. These di-block copolymers can have different ratios of PEG:polymer (w/w), such as but not limited to 5:1 to 1:1 (w/w) and a total size of about 200 Da to about 15 kDa, even preferably 400 Da to about 12 KDa, or even preferably 5 kDa to about 10 KDa. Alternatively, when used in this context, i.e., to be used as both plasticizer and the at least one polymeric material, the di-block copolymers can have a total size from about 15 kDa to about 25 kDa, such as 15, 16, 17, 18, 19, 20 21, 22, 23, 24 or 25 kDa. Should such copolymers be used both as stabilizer and as plasticizer/polymer, they are preferably present in the filament, and thus in the final implantable drug delivery device, in a total amount of about 55 to 85% (w/w), or even preferably in a total amount of about 60 to 80% (w/w), or even more preferably in a total amount of about 62 to 75% (w/w) such as 62, 63, 64, 65, 66, 67, 68, 69, 70, 71, 72, 73, 74 or 75% (w/w).

It is understood that in any case the sum of the percentages of all the components of the powders, filaments, and thus in the final implantable drug delivery device, reaches 100%.

In the context of the whole disclosure, when printed, the implantable drug delivery device is printed using a layer thickness from about 50 μm to about 500 μm, preferably from about 100 μm to about 400 μm such as 100, 125, 150, 175, 200, 225, 250, 275, 300, 325, 350, 375 or 400 μm. The implantable drug delivery device can be designed with an infill from 0 (hollow object) to 100% (full solid object). In an embodiment, the implantable drug delivery device comprises at least one internal hollow cavity. In an alternative embodiment, implantable drug delivery the device is a fully solid object.

In a further embodiment, the present invention relates to a process for producing an implantable drug delivery device, the process comprising:

i. cutting the filament as herein described at the appropriated length;
ii. moulding the filament as herein described until the delivery device as the appropriated form;
iii. pelletizing the filament as herein described until the delivery device as the appropriated form; or
iv. grinding the filament as herein described to obtain a powder with a suitable particle size distribution. If needed, this powder can be future coated to modify its wettability and better control the release rate of the active. The resulting powder can be also compressed or introduced in a classical drug formulation, such as a capsule.

An exemplary formulation for a filament according to the invention comprises about 30% of antibody, about 1.6% of excipients (including a low MW diblock copolymer, such as JH075, and buffer), about 6% of PEG, about 40% PLGA and about 20.4% of high MW diblock copolymer (such as a PEG 2k-P(d,l)LA 20k). A further exemplary formulation for a filament according to the invention comprises about 30% of antibody, about 1.6% of excipients (including low MW diblock copolymer, such as JH071, and buffer), about 6% of PEG, about 40% PLGA and about 20.4% of high MW diblock copolymer (such as a PEG 2k-P(d,l)LA 20k). A further exemplary formulation according to the invention comprises about 30% of antibody, about 1.6% of excipients (including low MW diblock copolymer, such as JH069, and buffer), about 6% of PEG, about 40% PLGA and about 20.4% of high MW diblock copolymer (such as a PEG 2k-P(d,l)LA 20k).

Preferably the formulations of the invention retain at least 60% of the therapeutic protein biological activity at the time of formulation and/or packaging over a period of at least 12 months (before the first use). The activity may be measured as described in the following section "Examples" or by any other common technics.

Herein also provided is a process for producing a powder or pharmaceutical composition in the dry state, the process comprising the steps of:

a. preparing a liquid pharmaceutical composition comprising or consisting of the active ingredient, at least one di-block or multi-block copolymer as herein described and optionally a buffering agent, at least one stabilizer and/or a surfactant, wherein said active ingredient is a therapeutic protein, b. freeze-drying or spray-drying the liquid pharmaceutical composition of step a to obtain the powder or the pharmaceutical composition in the dry state.

The invention also provides an article of manufacture, for pharmaceutical or veterinary use, comprising a container comprising any of the above described filament or implantable drug delivery device. Also described, a packaging material providing instructions for use.

The filaments or the implantable drug delivery devices of the invention may be kept for at least about 12 months to about 24 months. Under preferred storage conditions, before the first use, the formulations are kept away from bright light (preferably in the dark), at temperature from about 2 to 18° C., e.g., 18° C., 15° C. or at 2-8° C. The skilled person would understand that depending on the Tg of the polymer, the temperature of storage may be higher than 18° C., such as up to 25° C. (e.g., 20° C., 22° C. or 25° C.).

The present invention provides filaments and implantable drug delivery devices, for single use, suitable for pharmaceutical or veterinary use.

None of the pharmaceutical compositions, filaments, implantable drug delivery device or 3D printed implantable drug delivery device herein described comprise a disintegrating agent.

EXAMPLES

Figure 1:
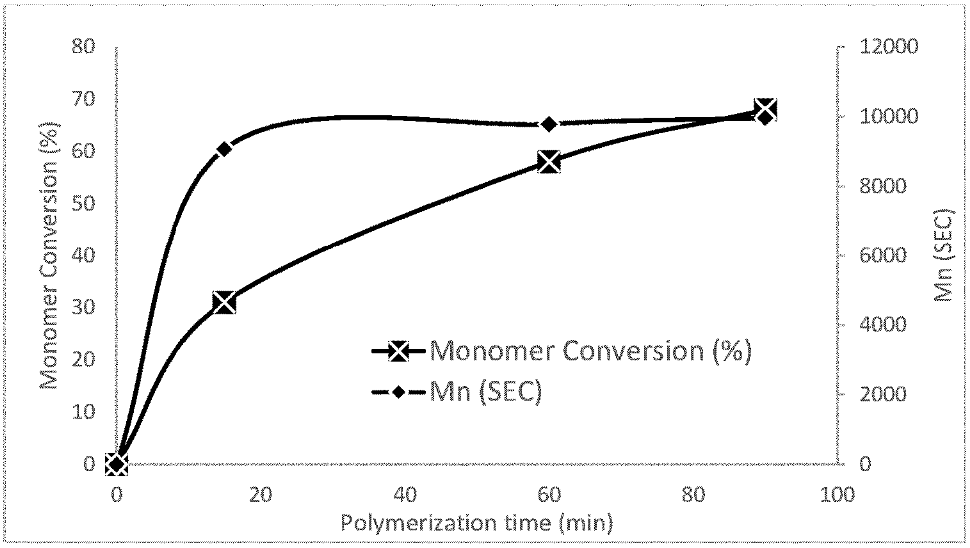
FIG. 1: Evolution with time of the monomer conversion and of the experimental Number average molecular weight (Mn) of the di-block copolymer PEG-P(d,l)LA (5 kDa-2.5 kDa) (JH073).

Abbreviations:

SD=spray-drying or spray-dried; HME=Hot melt extrusion; 3DP=Three-dimensional printing or Three-dimensional printed; DDS: Drug delivery system; DSC: Differential scanning calorimetry; DLS: Dynamic Light Scattering; Mw: Molecular weight; mAb: full length monoclonal antibody; PBS: Phosphate buffer solution; PEG: Polyethylene glycol; PEO: polyethylene oxide; PLGA: Poly(lactide-co-glycolide) acid; rpm: Revolutions per minute; Tg: Glass transition temperature; Tm: Melting temperature; Tc: crystallization temperature; SEC: size exclusion chromatography; TRE: Trehalose; % (w/w): Weight percentage (or weight/weight); Stab: stabilizer; STD: standard deviation; HLB Hydrophilic-to-Lipophilic Balance; Mn: Number average molecular weight.

1. Materials mAb1 is full length antibody of the IgG4 type, has a molecular weight (MW) of about 150 kDa and a pI of about 6.0-6.3.

2. Methods 2.1. Polymerisation of Di-Block Copolymers

The polymerisation was carried out in bulk on a batch mode following the reaction scheme reported by Regibeau et al. (2020). In brief, polymer synthesis was conducted in a batch mode within round bottom flasks equipped with two necks closed with rubber septum's and conditioned under dynamic nitrogen atmosphere. The requested PEG has been dried at 70° C. for overnight at about 2.10-2 mBar in order to eliminate water residue. Monomers, either D,L-lactide or D, L-lactide/glycolide mixture, were added under nitrogen atmosphere and melted at 130° C. Upon monomer melting, the catalyst solution of $Sn(Oct)_2$ was added in order to respect a monomer/catalyst molar ratio of 2000. The polymerization was carried out at 180° C. under magnetic agitation (300 RPM) for at least 10 min. After polymerization, $CHCl_3$ was added to the glass reactor to dissolve and recover the polymers. Purification of the polyesters was performed according to a dissolution/precipitation technique. Polymers were then dried at 65° C. under vacuum at ~$2.10^{-2}$ mBar during 12 h to eliminate residual solvent.

TABLE 1

Molecular features of the di-block copolymers and their corresponding codes

| Nature | Polymer batch code |
|---|---|
| PEG 2 kDa - P(d, l)LA 20 kDa | JH079 |
| PEG 2 kDa - P(d, l)LA 1 kDa | JH075 |
| PEG 5 kDa - P(d, l)LA 2.5 kDa | JH071 |
| PEG 5 kDa - P(d, l)LA 5 kDa | JH069 |

2.2. Spray-Drying and Freeze-Drying:

The excipients, i.e., trehalose or the di-block copolymer, were first dissolved in the antibody solution (50 mg/ml of mAb1 in a buffered solution) under lateral agitation (100 rpm) overnight at room temperature (RT). These solutions were then submitted to quench cooled freezing in liquid nitrogen, according to standard methods, for freeze-drying experiments. The spray-drying experiments was performed within Buchi R/D facilities in Essen (Germany) using a Buchi spray dryer, model B 290, according to standard methods. The weight of powder recovered after freeze-drying and spray-drying was determined in order to determine the yield of each drying method. The resulting powders were stored at 4° C., protected from water, under silica gel.

2.3. Hot Melt Extrusion

PEG 1500 and PLGA were first grinded with a Retsch grinder ZM 200 at 18000 rpm at RT using a grid of 2 mm. Just before proceeding to the HME, the PLGA polyester, PEG 1500 and the various powders were blended under orbital mixing for 1 hour using a Reax 2 overhead shaker (speed 3-4), Heidolph Instruments. The hot melt extruder device was a corotating twin-screw extruder from Thermo Fisher (Thermo 11). To limit extrusion duration, the powder feeding was realized in zone 5, adopting feed screw elements from zones 5 to 8. The degassing zone was replaced by a solid zone in view to prevent any polymer leak. The solid feeding was performed manually. Polymers were extruded through a die aperture of 2 mm diameter. The extrusion was performed within a temperature ranging between 45 to 75° C. at 40 rpm in order to avoid exceeding a torque value to 30%. The extrudate polymer was cooled down on an air-cooling bench (Pharma 11 air cooled conveyor).

2.4. Analytical Methods $^{1}$H.NMR: This method was used to measure monomer conversion. In brief, 15 mg sample was dissolved in 900 μL $CDCl_3$. Proton NMR spectra were acquired with a 400 MHz Bruker equipment (16 scans) adopting tetramethyl silane (TMS) as internal reference. 1H.NMR spectra were analyzed with MestReNova software. Monomer conversion was calculated from the area ratio of resonance peaks of the methyl or methylene protons of polymer and monomer. In particular, the methyl proton peak [5.26-5.12] ppm for PDLLA and [5.05-5] ppm for D,L-lactide were adopted to determine the % of conversion of these two monomers. Glycolide conversion was analysed using the methylene proton peak found at [4.90-4.60] ppm for PGA and [4.95-4.93] ppm for glycolide. Conversion values were calculated before and after elimination of residual monomer under vacuum. Means and standard deviations (STD) related to monomer conversion were calculated from at least two aliquots taken for each batch synthesis.

Differential scanning calorimetry (DSC): Thermal properties of polyesters were assessed by DSC performed with a Perkin Elmer Pyris 1 equipment. A 3 mg sample was cooled from room temperature to −20° C. at 20° C./min and held 5 min at this temperature. The sample was then heated at a rate of 20° C./min according to two temperature cycles adapted for each polymer composition. Glass transition temperature (Tg), crystallization temperature (Tc) and melting temperature (Tm) were calculated from the second heating step. These thermal tests were performed before and after residual lactide elimination for polyesters synthesized by reactive extrusion and only after lactide elimination for batch polyesters. In addition, for polyesters synthesized by reactive extrusion, DSC analysis was performed on samples recovered after reaching equilibrium state within the extruder. Means and standard deviations (STD) related to thermal properties were calculated by performing two DSC analysis for each experimental condition.

Molecular weight analysis of polyesters by size exclusion chromatography (SEC): Number average molecular weight (Mn), weight average molecular weight (Mw), and polydispersity index (Mw/Mn) of polyesters were measured by size exclusion chromatography (SEC) performed in chloroform at 30° C. adopting a Waters Millenium equipment. A 15 mg sample was dissolved in 3 mL of $CHCl_3$. Chromatographic separation was realized at a flowrate of 1 mL/min. A refractive index detector was used (Waters, model 2410). Relative molecular weights (number and weight average) and polydispersity index were calculated by reference to a polystyrene standard calibration curve established using the same experimental conditions. Means and standard deviations (STD) related to molecular weights and polydispersity were calculated as detailed above for NMR analysis.

Solubility assessment of the di-block copolymer in water: Di-block copolymers were dispersed in water at a concentration of 0.2 mg/mL at room temperature under magnetic agitation for 24 h. The solubility aspect of the dispersions has been recorded based on macroscopic observations, completed by Dynamic Light Scattering characterization (DLS) and SEC-MALS analysis.

SEC-MALS analysis: Antibody samples were dissolved at a concentration of 1 mg/mL in the mobile phase (200 mM phosphate buffer; pH 7) for 2 hours under lateral agitation at room temperature. They were injected on a TSK gel 3000 SWXL column at a flow rate of 1 mL/min at 30° C. and analyzed using a UV detector fixed at a wavelength of 280 nm. Detection of the synthetic polymers was performed by adding a Wyatt Optilab refractive index and a Wyatt Dawn MALS light scattering detector.

Density and diameter of the HME filaments: The diameter of HME filaments (sample segment of 10 cm length at least) was measured at 5 different sites of HME filaments with a High-Accuracy Digimatic Micrometer from Mitutoyo. The weight of this HME filament was measured with an analytical balance (precision: 0.01 mg). The length of the filament was measured with high precision calliper from Mitutoyo. From these three parameters density of HME filament has been calculated.

DLS analysis of the diblock copolymer solutions with or without the antibody: Antibody powders were dissolved in triplicate at two concentrations (1 and 10 mg/mL) under lateral agitation for 24 hours. Samples were analyzed by DLS using a Zetaziser Nano ZS at 173° 1 hour and after 24 hours after dissolution onset.

Antibody Recovery assessment by UV: Antibody samples were dissolved within 5 ml of water under agitation for 2 hours at room temperature. UV absorbance at 280 nm was determined using a Perkin Elmer Lambda 2 spectrometer. Antibody concentration was determined by reference to a calibration curve realized using antibody solutions with concentration ranging from 5 to 200 μg/mL. All solutions were performed in triplicate. The concentration of antibodies recovered was derived from the calibration curve, keeping into account the wt % of excipients in the experimental powders.

FTIR analysis of antibody powders: The chemical composition of the antibody powder was analysed by FTIR spectrometry using a Shimazu IRAffinity-1S equipment. The spectra were acquired in a range of 400 to 4000 $cm^{-1}$ using 16 scans and a resolution of 4 $cm^{-1}$. These analyses were performed in the ATR mode adopting the QATR™ 10 Single-Reflection ATR Accessory with a Diamond Crystal.

Static Mechanical testing of the HME filaments: Mechanical tests under static traction solicitation were carried out on HME filaments in order to assess the influence of the di-block copolymers and of the antibody on the cohesiveness and homogeneity of our formulations at a macroscopic scale. These tests were carried out on samples of at least 10 cm length. These traction tests were performed at room temperature with a traction bank Lloyd LRX PLUS, up to the rupture, using a preload of 1 N for placebo and samples loaded with antibody respectively, and considering deformation rate of 100 mm/min.

Solubility study of the antibody after HME processing: The dissolution kinetics of the antibody from HME pellets was studied by incubating about 30 mg of pellets in 1 mL of 200 mM phosphate buffer pH 7.0. The incubation was performed at 37° C. under stirring at 600 rpm using a Thermomixer Comfort® tubes mixer (Eppendorf AG). At predetermined time intervals, the samples were centrifuged during 15 minutes at 3000 RCF. The supernatant (1 mL) was collected in 1.5 mL Eppendorf and filtrated on a Pall Acrodisc® LC 13 mm syringe filter with 0.45 μm PVDF membrane.

The pellets were then suspended again in 1 mL of fresh 200 mM phosphate buffer pH7.0 solution for further dissolution. The filtrated supernatant was analysed by SEC-HPLC to determine the fraction of antibody released and measure the quantity (in %) of antibody aggregates contained in the sample.

Example 1—Design of Low Molecular Weight Di-Block Co-Polymers Made of PEG-P(d,l)LA, as Suitable Excipients of Biopharmaceutical Drugs Water solubility of the di-block copolymers was one of the critical specifications to fulfil in order to adopt them as excipients to stabilize biopharmaceutical drugs. The global chain length, the molecular weight fraction of the hydrophilic segment, the length ratio of the hydrophilic and hydrophobic segments, but also the nature and length of the polyester segment are important factors impacting the solubility or aggregation behaviour of copolymers in aqueous medium. Former studies highlighted that with PEG fraction <25 wt %, di-block PEG-PLGA formed nanoparticles or microparticles. Raising their hydrophilic/lipophilic balance with PEG fraction between 25% to 45%, self-assembled aggregates were generated. With a PEG fraction above 45 wt % the copolymers were under the form of micelles in water.

As the functionality expected from these di-block copolymers was to enhance their interaction with proteins, micelle formation has to be limited to prevent polymer interaction at the expense of polymer-protein interactions. In order to have more hydrophilic block-copolymers, three low molecular weight di-block copolymers made of P(d,l)LA sequence and characterized by PEG content equal to 50 or 67 wt % (see Table 1) were investigated.

TABLE 1

Composition (mean length of PEG and P(d, l)LA) and characteristics of the synthesis of hydrosoluble di-block co-polymers of PEGO-P(d, l)LA investigated.

| Batch code | Targeted Di-block sequences | % monomer residue before dialysis | Mn before dialysis | % monomer residue after dialysis | Mn—IP (SEC) |
|---|---|---|---|---|---|
| JH069 | PEG 5000-PDLA 5000 | 15 | 8600 | 1 | 8800-1.40 |
| JH071 | PEG 5000-PDLA 2500 | 51 | 6500 | 3 | 6500-1.20 |
| JH075 | PEG 2000-PDLA 1000 | 14 | 2800 | 1 | 2750-1.10 |

The evolution of the monomer residue content and molecular weights were assessed before and after their purification by dialysis conducted against water. A kinetic study of the polymerization of di-block copolymer PEG-P(d,l)LA (5 kDa-2.5 kDa) was conducted on a 90 min duration. The evolution over time of the monomer conversion and of the experimental molecular weight of the di-block copolymer (See FIG. 1), showed that the kinetics of polymerization was slower compared to the reaction rates typically observed for higher molecular weight copolymers. Moreover and surprisingly enough, the Mn reached a maximal value close to 10 kDa 20 min after the onset of the reaction, whilst the monomer conversion continued to increase during the time course of this study (90 min). The polydispersity index (data not shown) remained unchanged for the 3 polymerization batches and very low, i.e., 1.11. This promising result is indicative of the absence of trans-esterifications which could obviously occur during such a long period of reaction carried out at 160° C.

To eliminate the excess of lactide monomer, the di-block-copolymers were further purified by dialysis of their aqueous solutions conducted against water using membrane of a cut-off of 1000 Da. This additional step did not affect significantly the molecular weight of the di-block copolymers.

Figure 2:
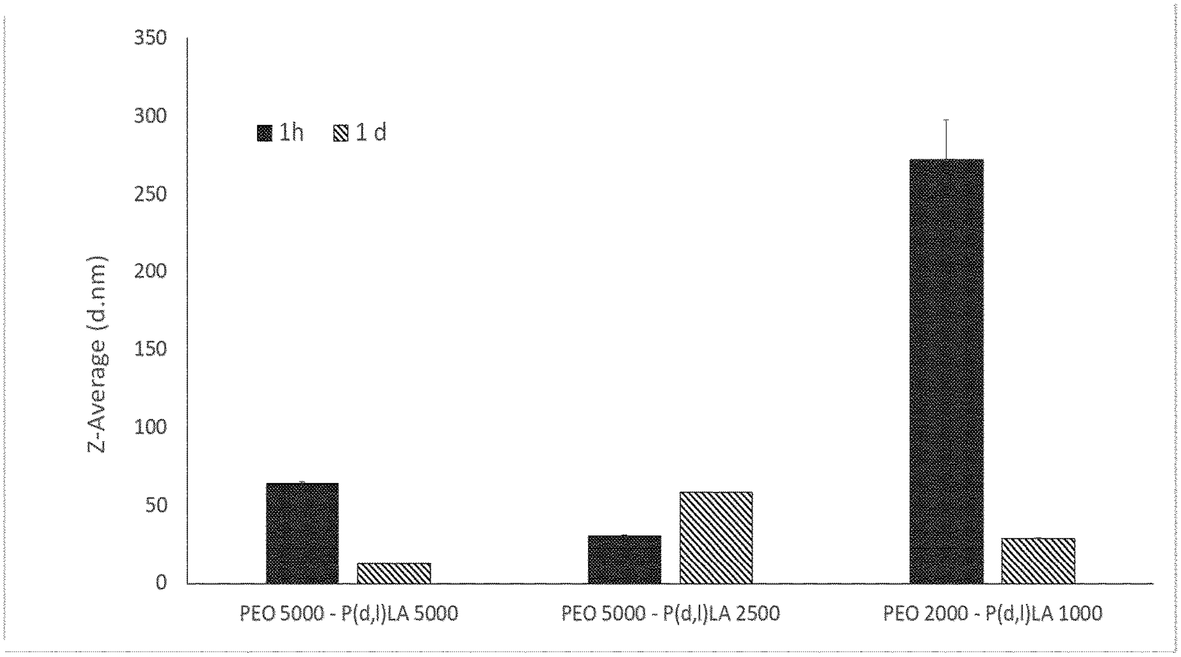
FIG. 2: Mean size of the di-block copolymers solubilized in water (at 10 mg/mL) at a temperature of 25° C. These DLS analysis were performed 1 h and 1 day after polymer dissolution.
Figure 3:
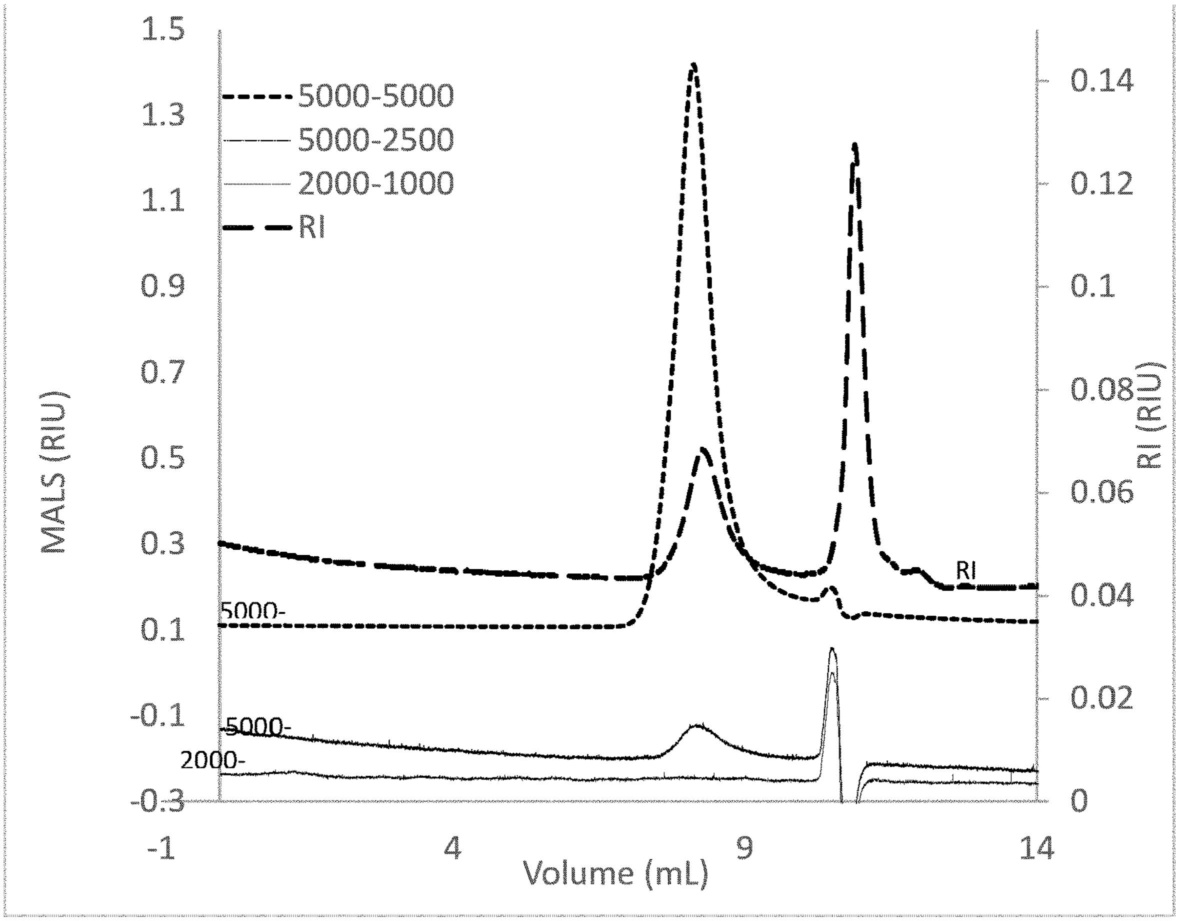
FIG. 3: SEC-MALS chromatograms of the di-block copolymers solubilized in water (at 10 mg/mL) at a temperature of 25° C. The MALS signal (given here at) 90° were reported for the 3 copolymers. The Refractive Index (RI) was given only for the di-block copolymer PEG-P(d,l)LA 5000-5000.

The solubility behaviour of the di-block PEG-P(d,l)LA co-polymers was analysed by DLS and SEC-MALS in order to verify their solubility in aqueous medium in an expected concentration range suitable to use them as excipient in antibody-containing formulations. The solubility of the di-block copolymers was assessed at a concentration of 10 mg/ml (before drying step). The dissolution state of these copolymers has been verified by DLS (FIG. 2) and SEC-MALS (FIG. 3). Once dissolved, in water at 10 mg/mL the 3 copolymers gave rise to a clear autocorrelation curve well discriminated from the light scattering noise. After deconvolution of these curves acquired at 25° C. at 175° angle, the mean size of polymer aggregates ranged from 30 nm to 270 nm after 1 h and between 15 nm and 63 nm after 1 day of dissolution.

The SEC-MALS chromatograms of the di-block copolymers, as shown in FIG. 3, highlighted a peak which was eluted at very short elution volume, with a mode close to 8.0 mL. This peak corresponds to a very high hydrodynamic diameter species with a molecular weight (Mn) estimated by MALS to be around $2.5\times10^6$ Da. Characterized by a high MALS/RI surface ratio, its intensity is significantly affected by the copolymer composition sequence. Indeed, the di-block copolymer PEG-P(d,l)LA 5000-5000 (JH069) also disclosed an intense signal in MALS, well detectable in RI. By comparison only a peak was observed for JH071. For the lowest Mw copolymer (JH075), only a slight deviation of the light scattering signal could be differentiated from the baseline. The MALS signal evolved in line with the expected increase in HLB and macromolecular features of the di-block copolymers and could therefore be assigned to polymeric micelles. Accordingly, JH069, made from PEG 5 kDa-P(d,l)LA 5 kDa, thus characterized with the longest length of polymer blocks and with the lowest weight fraction of PEG (50%) should be prone to micellisation. JH075 and JH071, characterized by a high PEG content of 67 wt % and low molecular weight should be nearly freely soluble in aqueous medium.

Example 2—Evaluation of the Stabilization Efficiency of the Di-Block Copolymers During Drying of an Antibody Solution Either by Freeze-Drying, or by Spray-Drying The efficiency of the di-block copolymers to stabilize an antibody was assessed using spray-drying and freeze-drying.

Because of the different physico-chemical stresses met during these two drying methods, they were compared in terms of stability of mAb1. If spray-drying is more attractive for scale-up purpose in the industry, this methodology typically generates a lot of interphases, under the form of a liquid lair interphase during the nebulization step, and solid/air interphase during the evaporation step, possibly leading to the main source of protein denaturation.

TABLE 2

Composition of the antibody formulations submitted either to spray-drying or freeze-drying as suggested by the full factorial design software (JMP from SAS).

| Copolymer type and batch | Wt % of copolymer: mAb1 | Wt % of trehalose: Antibody |
|---|---|---|
| PEG-P(d, l)LA 2000-1000 (JH075) | 20 | 5 |
| | 5 | 20 |
| | 20 | 20 |
| | 5 | 5 |
| PEG-P(d, l)LA 5000-2500 (JH071) | 20 | 5 |
| | 5 | 20 |
| | 20 | 20 |
| | 5 | 5 |
| PEG-P(d, l)LA 5000-5000 (JH069) | 20 | 5 |
| | 5 | 20 |
| | 20 | 20 |
| | 5 | 5 |
| Control | 0 | 0 |
| | 0 | P |
| | P | 0 |

* P: For these two controls, the amount of excipients, either the copolymer, either the trehalose, has been fixed to be equivalent to the formulations detailed above, but without antibody.

The composition of the formulations reported in Table 2 were coded using "C" and "Ex" for copolymer and trehalose respectively. These codes have been preceded by the respective wt % of these two products in the formulation. Accordingly and as an example, the composition labelled "5C 5Ex" later in this example and in the Figures stands for a formulation containing 5% of copolymer and 5% of trehalose.

The stabilising efficiency of the di-block copolymer was evaluated based on their macromolecular features, their ratio (wt %) to the antibody, but also their proportion to trehalose, a low molecular weight sugar typically added for protein spray drying. In order to evaluate in a multiparametric way the influence of these parameters, a full factorial design software was used (JMP from SAS) The tested compositions are reported in Table 2. Additional controls were introduced, i.e., without trehalose or without any excipient at all, in order to evaluate respectively the effectiveness of the copolymers alone or to control the aggregation extent of the antibody after drying without adding any stabilizer.

The influence of the drying method and of the formulation composition was investigated comparing the morphology of the powder under scanning electron microscopy. Interaction between the antibody and the copolymer has been verified by FTIR spectroscopy. Further, the redissolution rate and status of the antibody have been monitored by Dynamic Light Scattering (DLS) and quantified by SEC chromatography in terms of % of antibody aggregates and fraction of antibody redissolved.

Figure 4:
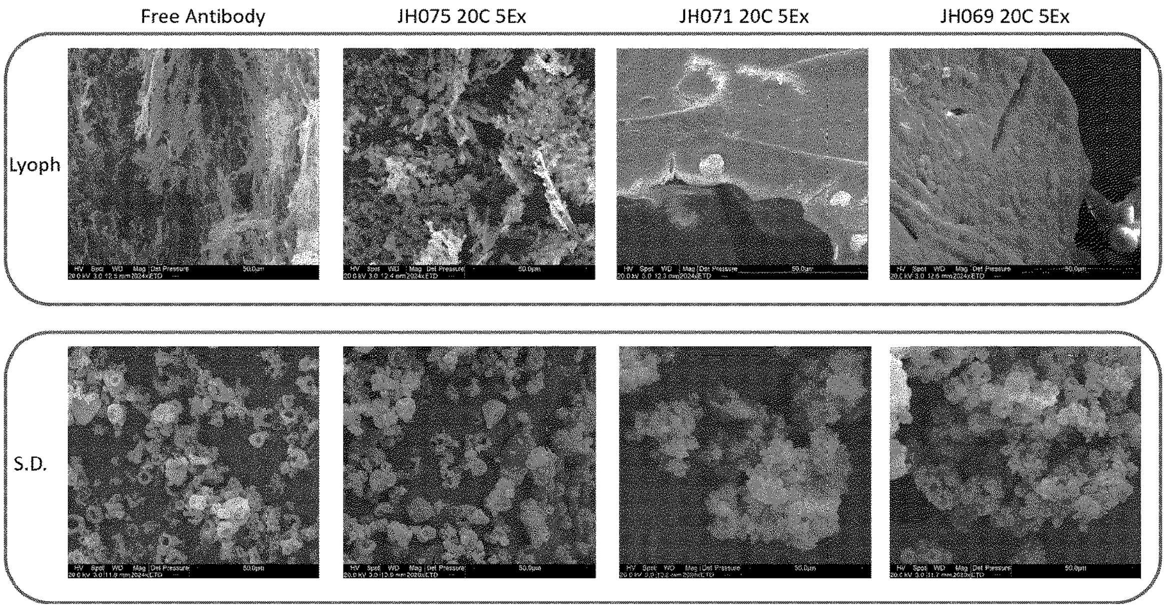
FIG. 4: Comparison of the morphology of the mAb1 powders obtained either after lyophilisation ("Lyoph") or after spray-drying ("S.D.") as a function of the excipient composition. SEM observations were performed adopting a Quanta 600 from FEI under a 20 kV acceleration voltage.

Morphology of antibody powders analysed by SEM (FIG. 4): It was observed that the powders' microscopic details were significantly affected by the drying process: freeze-drying generated porous foams while spray-drying produced particles or particle aggregates with a mean size ranging from 2 to 10 μm. This main difference in morphology of the powders was associated to a main difference in specific area, estimated to be in a range of 5 and 50 $m^2/g$ for freeze-dried and spray-dried products respectively. This difference in specific area between the two sets of powders is directly translated in terms of electrostatic properties observed during SEM observations. Despite the fact that all samples were metallized with silver before performing the microscopic observations, most of the pictures taken for spray-dried powders were of lower quality with too much contrast and lack of details in the microstructure of the powders. In contrast the SEM pictures acquired on the powders obtained after freeze-drying had a better resolution whatever the magnifications adopted.

All spray-dried formulations comprising copolymers disclosed quite similar morphology with particles relatively homogeneous in size (mean size around 10 μm) with a disk shape behaviour and a biconcave aspect. This morphology was similar for the free antibody used as control (i.e., obtained by spray-drying the antibody solution in the absence of any excipient). The only morphological change was a more pronounced agglomeration of the particles, which appears to be correlated with the increase in molecular weight of the copolymers. This observation suggested that the copolymer had a very limited action on the morphology of the powders.

In contrast the powders obtained after freeze-drying disclosed very different morphologies in function of the composition of the formulations. In the absence of any excipients the resulting freeze-dried powders had very high and open porosities with a fibrous-type architecture. Due to the expected fragility of this structure, broken fragments were noticed in some fields of this sample. In the presence of the copolymer JH075/20C 5Ex, the antibody powder was more cohesive and was mostly made from homogeneous particles with a size around 5 to 10 μm which were aggregated. The most drastic changes in powder morphology were noticed when increasing slightly the molecular weight of the di-block copolymer. Indeed, when the antibody solution with stabilised either with JH071 or JH069, the freeze-dried powders were mostly not porous with a resulting material denser and more cohesive. These observations supported the effects expected during lyophilisation, i.e., to act as bulking or texturing agent to prevent shrinkage and cracking of amorphous cake, leading to a stabilised formulation.

FTIR analysis of antibody powders: to verify a possible interaction between the antibody with the di-block copolymers in function of the excipient composition during spray-drying or freeze-drying, FTIR spectra of the formulations were compared to the theoretical spectra of their individual components, i.e., the antibody (without excipient), the block copolymer and trehalose, divided by their weight fraction. This comparison highlighted two spectroscopic changes supporting the existence of interactions between our block copolymers and the antibody after drying. Firstly, a change in the intensity signal of the polyester and polyether segments in FTIR (data not shown). Indeed for all compositions evaluated, whatever the drying method and the block-copolymer, the FTIR spectra were mostly dominated by the specific peaks of the antibody. In contrast the C═O stretching band of the polyester segment and the $CH_2$ were mostly masked by the protein signals. Further, a slight shift was noticed for the N—H bending vibration and N—N stretching (Amide II) for most of the formulations, compared to the peak for the free antibody (data not shown).

Dissolution kinetics of the antibody powders: The comparison of the redissolution of the antibody in function of the drying process revealed that in contrast to spray-drying, the dissolution of the freeze-dried antibody proceeded very quickly (thus within maximum 1 h), giving rise to a mean size of protein solution between 15 to maximum 52 nm when dissolved at 10 mg/mL in water at room temperature and whatever the compositions of the formulations. After spray-drying, the DLS analysis clearly highlighted that the redissolution of the antibody was affected by the composition of the excipients. 1 h after the dissolution onset, the mean size of most of the dried formulations are above 100 nm. The copolymer composition was however affecting the antibody dissolution. Indeed, in the presence of the copolymer JH069, a more significant disaggregation of the antibody was noticed compared to the two other di-block copolymers.

Figure 5:
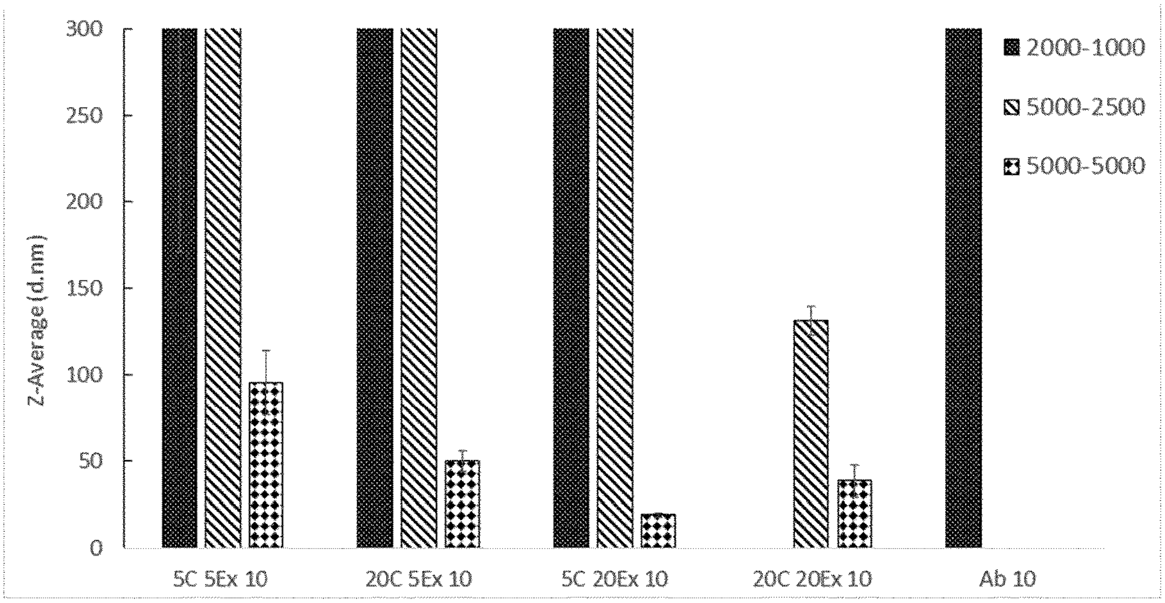
FIG. 5: Comparison of the mean size (DLS) of the mAb1 powders prepared with the 3 copolymers after solubilization (at 10 mg/mL) in water, 1 h after dissolution of the spray-dried powder (A) or freeze-dried powder (B).
Figure 5:
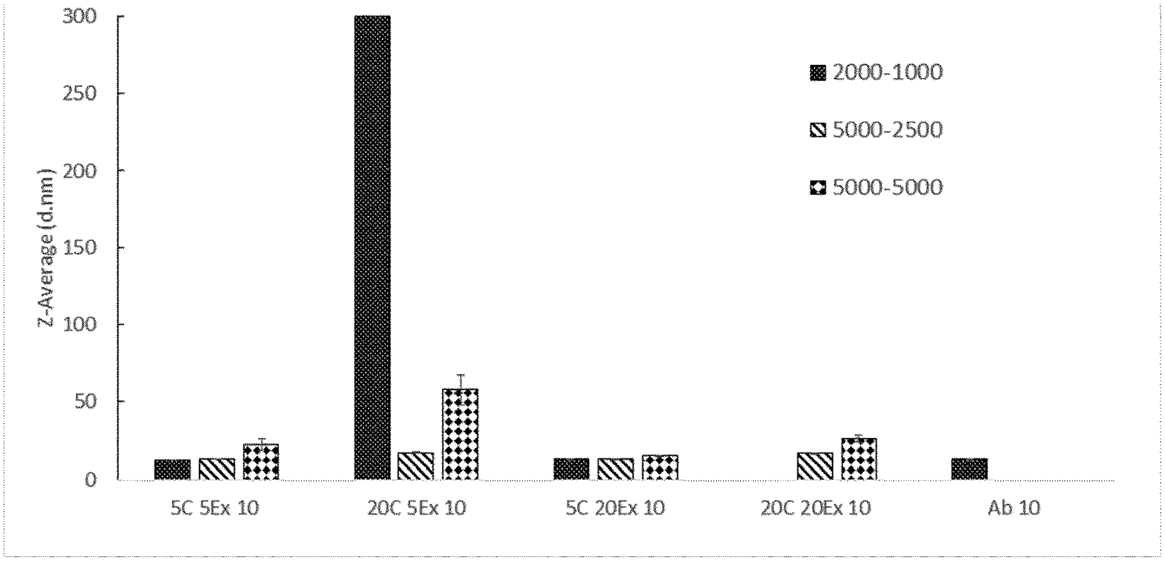

As shown in FIG. 5, after 1 day of dissolution, exception made of the formulation 20C 5Ex based on JH075, all antibody solutions have a mean size in DLS between 15 to 52 nm.

From these observations, it was concluded that:

The aggregation of the antibody was promoted by the spray-drying process compared to freeze-drying process, as expected from the higher specific surface generated during drying and/or of the thermal stress imposed.

The PEG-P(d,l)LA di-block copolymers were able to enhance antibody dissolution after spray-drying. This physico-chemical protection action is a function of the copolymer properties, i.e., of the respective length of PEG and polyester segments. Indeed, the copolymer with the lowest HLB, thus more prone to produce micelles, acted more efficiently to redissolve the antibody after spray-drying.

UV-SEC analysis of the antibody before and after drying: The efficiency of the di-block copolymer as a stabilizer excipient has been evaluated playing on their macromolecular features, their wt % ratio to the antibody, but also their proportion to trehalose. Additional controls have been introduced for these compositions, i.e., without trehalose or without any excipient at all, in order to evaluate respectively the effectiveness of the copolymers alone or to control the aggregation extent of the antibody after drying without adding any stabilizer.

Figure 6:
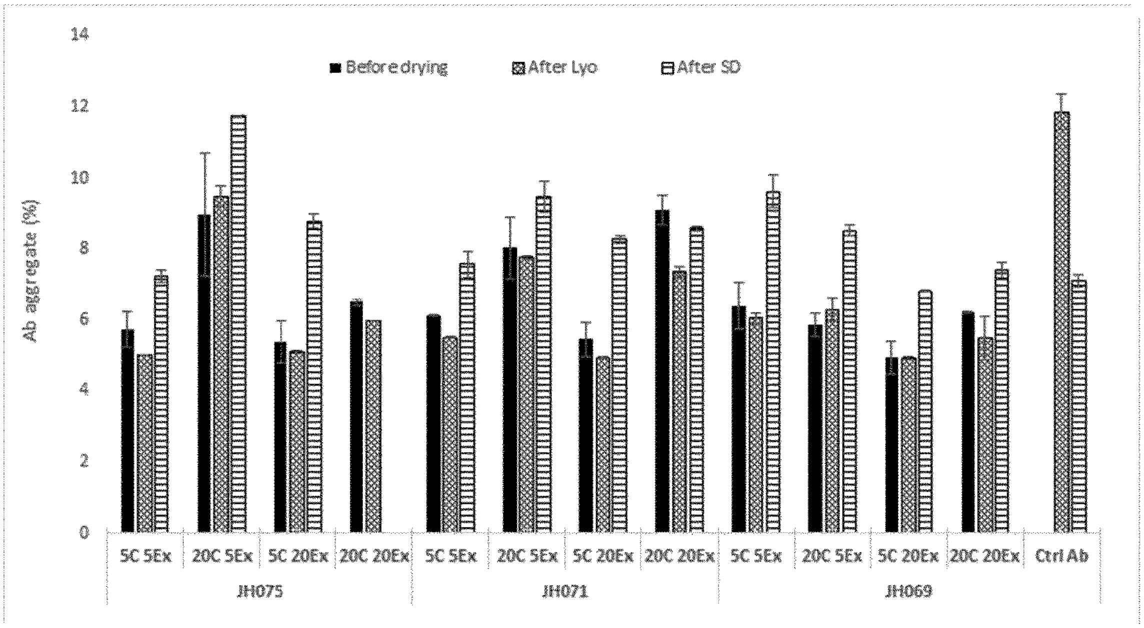
FIG. 6: Comparison of the percentage of mAb1 aggregates as a function of the drying conditions, copolymers and excipient compositions.

As shown in FIG. 6, exception made of the control, for all compositions evaluated, the percentage of antibody aggregates is 5 to 15% higher after spray-drying compared to the freeze-dried samples. Under the tested conditions, it seems that the spray-drying methodology generated more physico-chemical stress compared to lyophilisation. The presence of di-block copolymers as an excipient during freeze-drying process provided a clear benefit. Indeed, without them the percentage of antibody aggregates is 11.86% (control), a value about twice compared to the mean % observed for the formulations containing di-block copolymers (6.15%). In contrast using spray-drying the lower values of antibody aggregates were observed with respect to the control (without excipient) and in the presence of the higher Mw of the di-block copolymer JH069 (between 6.82 and 9.62%). Some of the formulations promoted the aggregation of the antibody after lyophilisation. This elevation of antibody aggregates was mostly observed with the control formulation (i.e., without any excipient i.e., 11.86%, compared to the di-block copolymer formulations: JH071 (20C 20Ex): 9.09%>JH075 (20C 5Ex): 8.97%>JH071 (20C 5Ex): 8.03%. In contrast the lower values of antibody aggregates were observed in the presence of the higher Mw of the di-block copolymer JH069 (between 4.92 and 6.29%).

Antibody Recovery assessment by UV: The soluble fraction of the antibody was measured by UV without proceeding to any filtration and fractionation by chromatography in order to avoid any adsorption which could result from these two purification steps. The data reported in Table 3 highlights that the antibody recovery is close to 100% whatever the drying method and the formulation compositions. The two exceptions correspond to the control, i.e., antibody solution which has been freeze-dried or spray-dried without any trehalose and/or block-copolymer. In these two cases, the antibody recovery is significantly lower, i.e., 60 and 85% respectively.

TABLE 3

Comparison of the antibody recovery determined by UV (280 nm) in function of the drying conditions and excipient compositions.

| | | Antibody recovery (%) | | | |
|---|---|---|---|---|---|
| Di-block | | After Spray Drying | | After Lyophilisation | |
| copolymer | Composition | Mean | SD | Mean | SD |
| JH075 | 5C 5Ex | 94.9 | 1.8 | 95.8 | 0.9 |
| | 20C 5Ex | 98.3 | 0.1 | 95.9 | 2.8 |
| | 5C 20Ex | 100.8 | 1.0 | 98.6 | 0.8 |
| | 20C 20Ex | ND | ND | 100.5 | 0.3 |
| JH071 | 5C 5Ex | 94.8 | 2.4 | 100.1 | 2.3 |
| | 20C 5Ex | 96.3 | 1.9 | 100.3 | 1.0 |
| | 5C 20Ex | 95.4 | 1.3 | 101.7 | 2.1 |
| | 20C 20Ex | 95.1 | 1.1 | 92.9 | 4.2 |
| JH069 | 5C 5Ex | 103.2 | 2.2 | 102.8 | 1.0 |
| | 20C 5Ex | 98.3 | 2.8 | 100.0 | 0.1 |
| | 5C 20Ex | 97.9 | 1.2 | 100.2 | 0.0 |
| | 20C 20Ex | 98.3 | 0.3 | 100.9 | 0.5 |
| control | Antibody alone | 89.0 | 6.9 | 62.0 | 4.0 |

A statistical analysis of the results (Antibody aggregate (%), Mean size (nm) and Antibody recovery (%) were considered) was performed by fitting the model (factorial degree 2 entering main effects and two-ways interactions) to data using a standard least-square minimization approach, then following a backward elimination approach in removing non-significant terms. The assumptions of the analysis of variance were verified on the residues: normality (normal quantile plot), homoscedasticity (residuals versus fits plots), and independence (time-series plot).

For the 12 formulations (excluding formulation without copolymer), a model fitted with all main effects and two-ways interactions was considered: type of co-polymer, % co-polymer, % excipient and step (before drying, after lyo, after SD).

Statistical analysis was performed at a significance level of 5% (alpha=0.05), which means that if p-value>alpha, then the estimated parameter is statistically equal to zero and therefore the term has no significant effect on the response variable at alpha level, while if p-value<alpha, then the estimated parameter is statistically different from zero and therefore the term has a significant effect on the response variable at alpha level.

The Coefficient of Variation or % Relative Standard Deviation (% RSD DoE) is computed as:

$$\% \text{ RSD DoE} = \text{RMSE}/(\text{Overall mean}) \times 100\%$$

where RMSE (Root Mean Square Error) is the square root of the variance of the residuals.

A positive effect of the tested parameters on a response means that an increase of this parameter leads to an increase of this response. On the contrary, a negative effect tends to a decrease of the response. Significant fitting models were obtained as follows:

- Aggregates: Aggregates (%) significantly increased with an increase in the % co-polymer (p value<0.0001). This effect was reinforced when using the JH075 and after spray-drying. To the contrary, the use of JH069 and lyophilization, in combination of a higher amount of excipient significantly reduced the antibody aggregates (%).
- Mean size measured by DLS (p value=0.0013). Significant effects were shown for JH071 and spray-drying, leading to an increase of the mean size especially at low level of co-polymer. Indeed, an increase of the co-polymer amount in the formulation induced a decrease of the mean size.
- Antibody recovery: Antibody recovery (%) was positively affected when using JH069 (p value=0.0215). On the contrary, the use of JH075 led to a decrease of the Antibody recovery. This effect was reduced at 20 Wt % of excipients. Once more, the spray-drying process led to the worst mAb1 recovery results.

Altogether, these results supported the efficiency of di-block copolymers to protect antibodies against aggregation during either freeze-drying or spray-drying.

Example 3—Evaluation of the Properties of the Di-Block Copolymers to Enhance Dispersion of the Antibody in HME Formulations-Redissolution Study of the Antibody In Vitro It was shown in Examples 1 and 2 that low molecular weight di-block copolymers of PEG-P(d,l)LA act as protein stabilizer during the drying step. It was anticipated by the inventors that they could also play the roles of i) compatibilizer between the polyester matrix and the protein, and ii) plasticizer to reduce the temperature during HME processing. Regarding this latter role, low molecular weight PEGs are indeed well-known to act as plasticizer of the degradable aliphatic amorphous polyesters such as PLGA or PDLA.

PEG-P(d,l)LA di-block copolymers were dissolved within an antibody solution (50 mg/mL of mAb1) using a 5 wt % proportion of copolymer. After freeze-drying, the resulting antibody powders were blended either with a PLGA (15 kDa) and PEG (1.5 kDa) or with the same copolymer as used for the FD step according to the formulation compositions outlined in Table 4, considering a drug loading of at least 20%.

HME filaments loaded with the antibody were successfully produced using only the combination of the low Mw di-block copolymers firstly added before lyophilisation and a high Mw di-block copolymers of PEG-P(d,l)LA (2 kDa-20 kDa) while working at a low temperature ranging from 70° C. to 75° C. (Series A). As expected by the inventors, the plasticizing action given by the PEG sequence of the di-block copolymers avoided therefore to add additional plasticizer, such as free PEG or triethylcitrate, which would also contribute to the total content of inert and water-soluble excipients susceptible to act as porogenic agents.

A HME filament control was realized adopting the antibody freeze-dried with low molecular weight excipients and blended with a high molecular weight di-block copolymer PEG-P(d,l)LA (2 kDa-20 kDa) to achieve a final drug loading of 30%.

Figure 7:
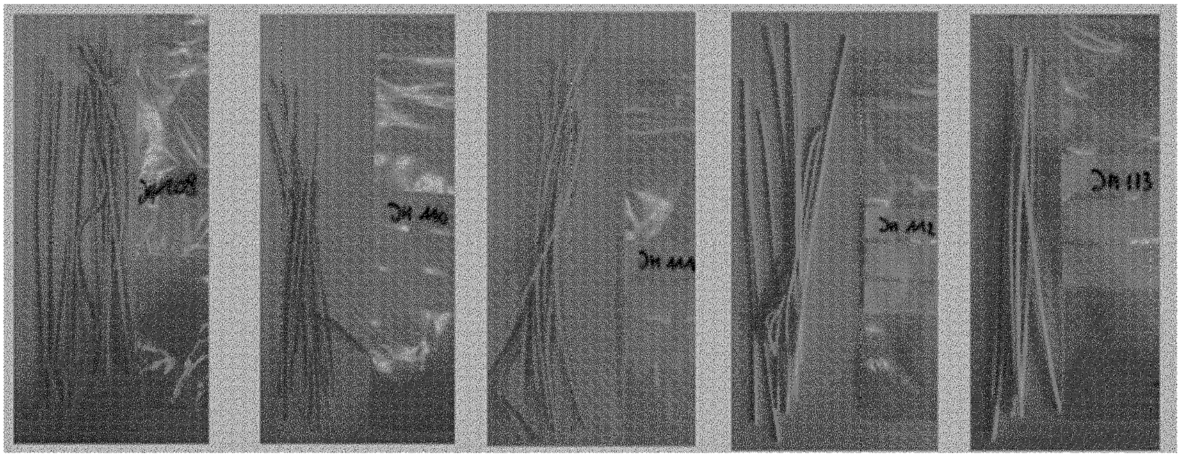
FIG. 7: Macrographies of some of the HME filaments loaded with the mAb1 according to the formulation compositions given on Table 4.

After extrusion via HME, regular filaments were obtained for all of the samples (see macroscopic pictures given on FIG. 7; filaments were regular in diameter, homogenous and have a white aspect).

Figure 8:
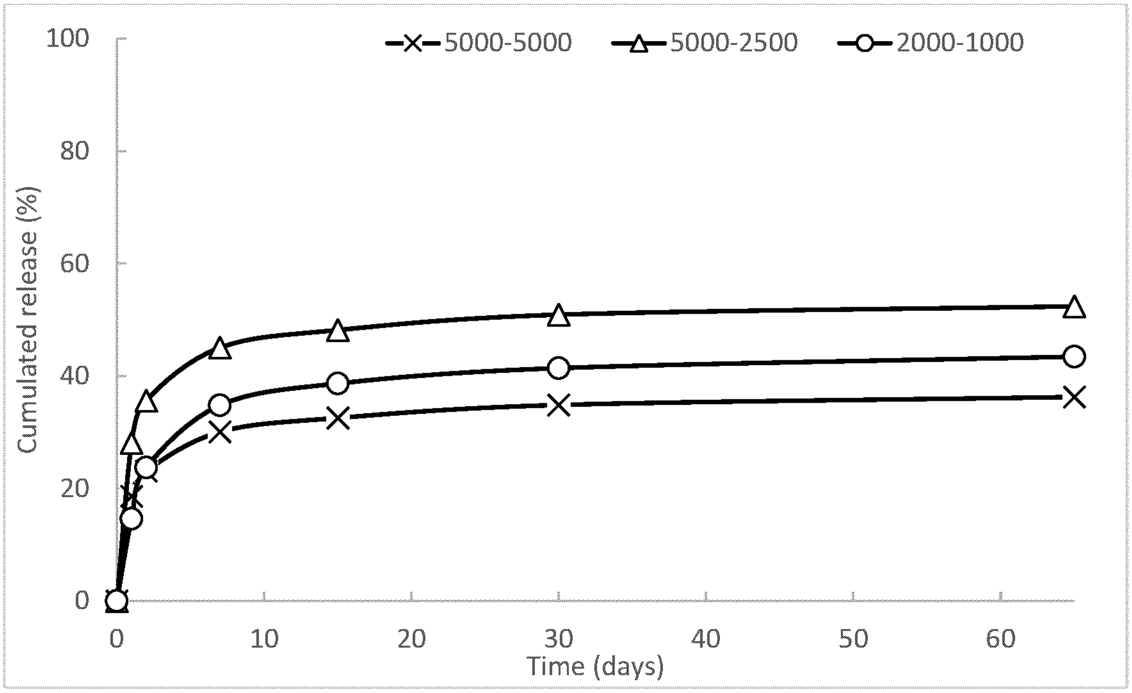
FIG. 8: A) In vitro release kinetics of mAb1 from HME filaments of the Serie A. B) In vitro release kinetics of mAb1 from HME filaments of Serie B. In both case the results are expressed in terms of % cumulative calculated from the total mAb1 loading.
Figure 8:
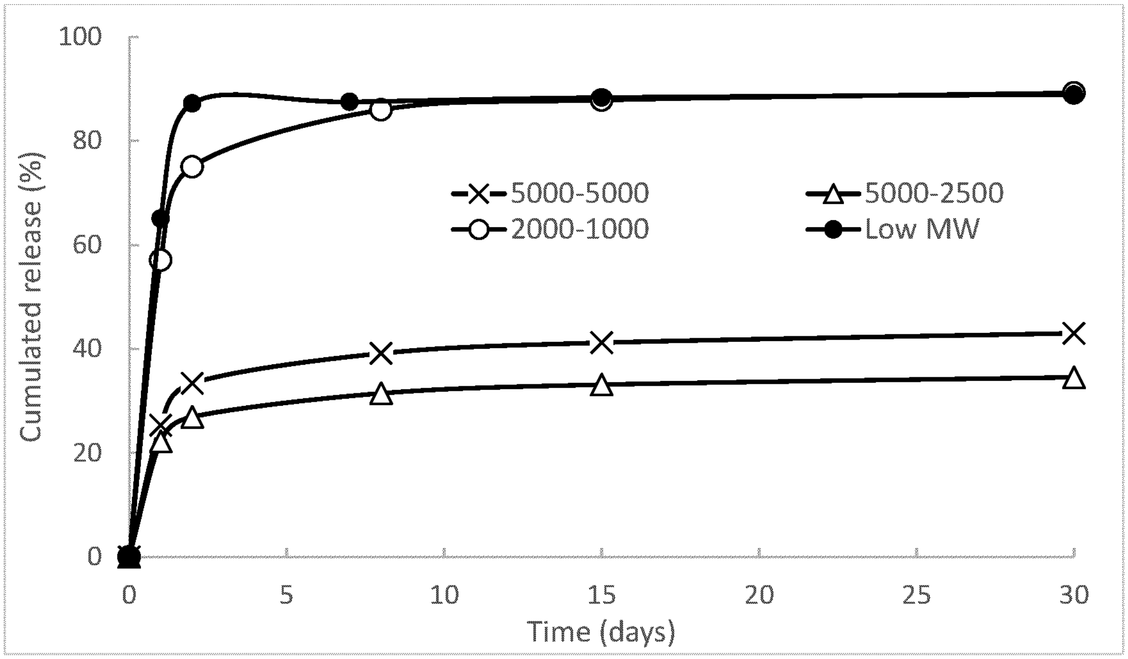
Figure 9:
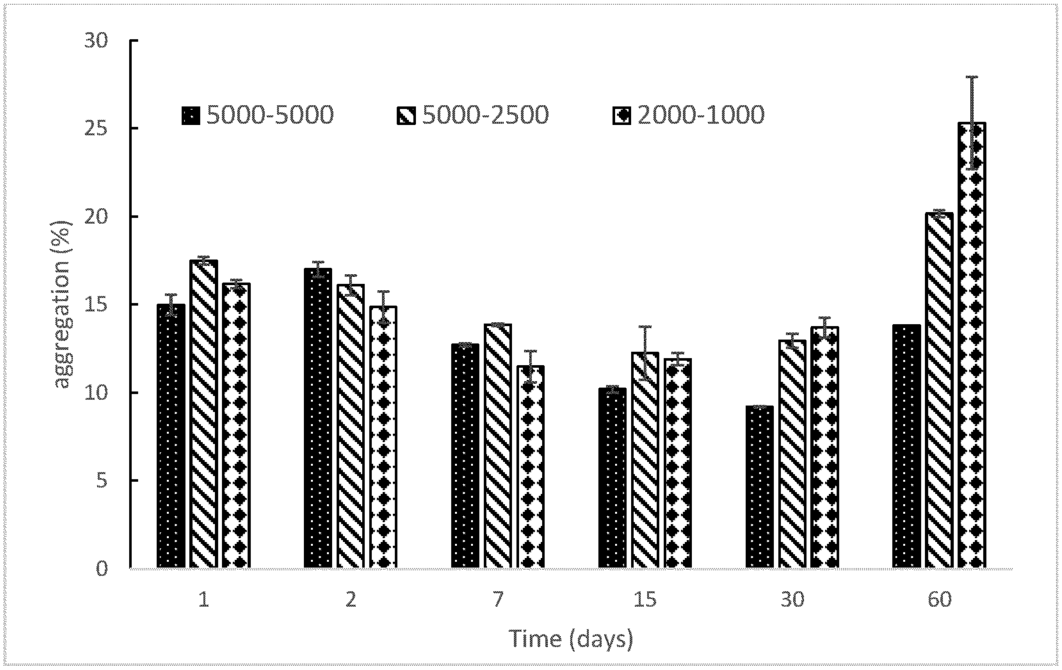
FIG. 9: A) Evolution with time of the % of aggregated mAb1 released in vitro from HME filaments of Serie A. B) Evolution with time of the % of aggregated mAb1 released in vitro from HME filaments of Series B. In both cases, the results are expressed in terms of % cumulative calculated from the total mAb1 loading.
Figure 9:
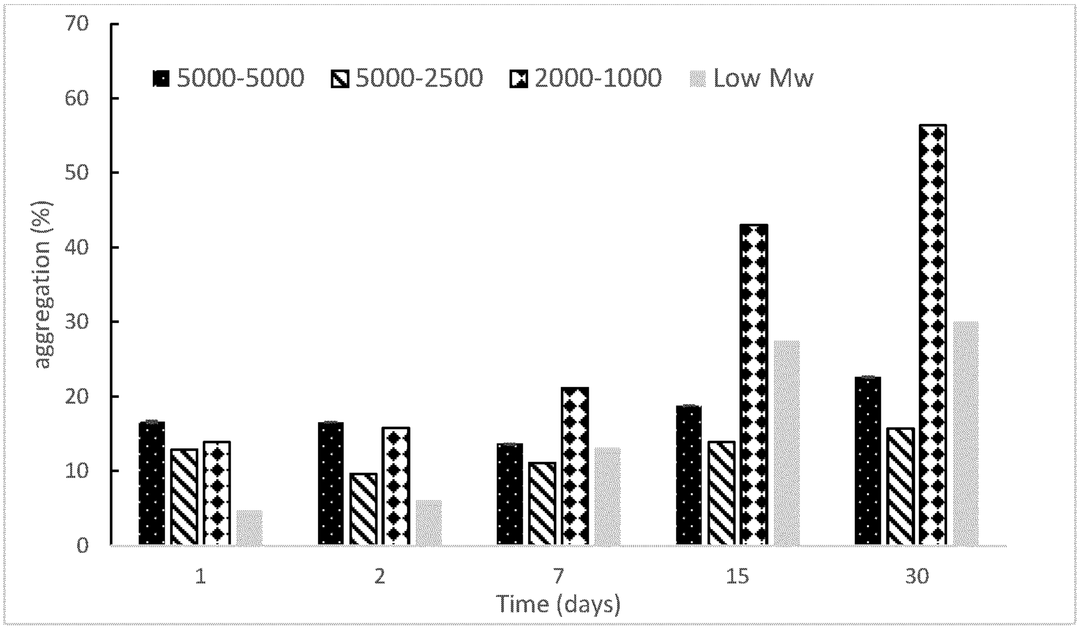

The in vitro release kinetics of the antibody from these HME filaments were measured at 37° C. in PBS. The fraction of antibody released in PBS were analysed by SEC-UV on one-month period (FIGS. 8 and 9). The antibody released from the JH113 filament loaded with antibody freeze-dried with the low Mw excipients proceeded very fast (very important and unacceptable burst). In contrast, the release of the antibody from any of the filaments JH105-JH111 loaded with mAb1, initially freeze-dried with 5 wt % of one the low Mw di-block copolymers PEG-P(d,l)LA, was progressive and sustained on a duration of at least 30 days (FIG. 8). Their release profiles were characterized by 2 phases, the first phase corresponded to a rapid release of the antibody over day 2 or day 3 and was followed by a slower dissolution of the protein from the polymer matrix up to at

TABLE 4

Compositions of the HME formulations. As excipient, either one of the 3 low molecular weight hydrosoluble copolymers (5%, See also Table 1) or classical low molecular weight excipients (30%) were used.

| HME batches | | Components of HME batches | | | | | |
|---|---|---|---|---|---|---|---|
| | | Excipient | | Composition (wt %) | | | |
| Batch No. | Serie | Nature | % Wt copolymer to antibody | PLGA (% Wt) | PEG 1500 (% Wt) | PEG 2k-P(d, l) LA 20k (% Wt) | Antibody and excipients (% Wt) |
| JH105 | Serie A | JH069 | 5 | **42.1** | 6 | 20.3 | 31.6 |
| JH106 | Serie A | JH071 | 5 | **42.1** | 6 | 20.3 | 31.6 |
| JH107 | Serie A | JH075 | 5 | **42.1** | 6 | 20.3 | 31.6 |
| JH110 | Serie B | JH069 | 5 | **0** | 0 | 68.4 | 31.6 |
| JH111 | Serie B | JH071 | 5 | **0** | 0 | 68.4 | 31.6 |
| JH112 | Serie B | JH075 | 5 | **0** | 0 | 68.4 | 31.6 |
| JH113 | Serie B | Classical Low MW (control) | 30 | **0** | 0 | 61 | 39 |

least 30 days. Interestingly enough the release kinetics of the antibody was affected by the composition of the low molecular weight di-block copolymers PEG-P(d,l)LA added as stabilizer during lyophilisation. Indeed, as highlighted on FIG. 8*a*, for HME filaments made with a ternary polymer blend made from PLGA, PEG (1.5 KDa) and the high molecular weight di-block copolymer PEG-P(d,l)LA (2 kDa-20 kDa) gave rise to slight, but significant, differences in release profile of the antibody (HME batches JH105, JH106 and JH107). The total fraction of protein released in the PBS after 60 days increased according to the following order of the di-block copolymer composition: 5 kDa-5 kDa<2 kDa-1 kDa<5 kDa-2.5 kDa.

The release profiles noticed for HME filaments composed only from the high molecular weight di-block copolymer PEG-P(d,l)LA (2 kDa-20 kDa) and of the antibody freeze-dried with the low molecular di-block copolymers (Serie B) also disclosed a biphasic release profile of the antibody (FIG. 8*b*). But in these cases, the nature of the di-block copolymers used as stabilizers during lyophilisation affected more the antibody-release kinetics and in a different way compared to the data disclosed for the Serie A. For Series B about 85% of the antibody was released after 7 days of in vitro dissolution of the HME filament made in the presence of the low Mw diblock copolymer PEG-P(d,l)LA 2 kDa-1 kDa. In contrast a slower release profile of the antibody was observed with HME filaments made in the same way and with the same composition exception made that the antibody has been lyophilized in the presence of one of the two more hydrophobic diblock copolymer PEG-P(d,l)LA, thus with composition of 5 kDa-5 kDa and 5 kDa-2.5 kDa. In these two cases between 20 to 30% of the antibody was released after 4 days of incubation of the HME filaments in PBS during the first phase of the release. Beyond this period, the antibody continued to be released, but at a rate 50 times lower than observed during the initial phase.

The percentage of antibody aggregates was not significantly impacted by the composition of the low Mw di-block copolymer used for freeze-drying and remained relatively constant, i.e., around 15%, over 60 days (FIG. 9*a*). This level of protein aggregation should be compared to the value observed in the original antibody solution (4.5%) and after its freeze-drying (between 5 and 9%). However, a significant increase in antibody aggregates was noticed in filaments obtained from formulations lyophilised with the lowest Mw di-block copolymer PEG-P (d,l)-LA (2000-1000) JH075. In contrast a lower content of antibody aggregates (between 4.5 and 6%) were noticed first in the release medium 1 and 2 days after the dissolution of the HME formulation made with the antibody lyophilized with the low molecular weight excipients. However, this % of antibody aggregates increased progressively to achieve values up to 60% after two months of in vitro incubation.

CONCLUSION

The efficiency of low molecular weight hydrosoluble di-block copolymers made of PEG-P(d,l)LA has been demonstrated in terms of:

- Stabilisation of a therapeutic protein (such as exemplified herein with an antibody) during drying, either by spray-drying or freeze-drying, allowing to exclude any other low Mw excipients (e.g., trehalose), and to decrease the total excipient content between 1 to 5%.
- Plasticizing and miscible action within aliphatic polyester matrices such as PLGA during hot melt extrusion.
- Ability to adjust the release rate of the therapeutic protein from HME filaments and to maintain a sustained release rate on an extended period of at least 2 months in vitro.

OVERALL CONCLUSION

Original water-soluble low-molecular weight di-copolymers made of PEG-P(d,l)LA sequences were successfully tailored to fine tune their water solubility and hydrophilic/lipophilic balance, playing on the respective lengths of the polyether to polyester segments. Thanks to their composition, macromolecular architecture and molecular weight, they were able to present at least the three following excipient roles during drying of a therapeutic protein (such as exemplified herein with antibodies):

- They acted as water replacement.
- They successfully provided bulking and cohesiveness to the final solid.
- They promoted the intimate mixing of antibodies within hydrophobic aliphatic polyester.

Moreover, using hot melt extrusion (HME) to blend the protein drug within the thermoplastic polymer, the PEG sequence of the di-block copolymer acted as plasticizer to reduce the temperature of processing, a critical aspect to avoid thermal degradation of biopharmaceutical drug. Adopting a drug loading as high as about 30% of antibody, the release rate of this pharmaceutical active was demonstrated to be progressive on a 2-month period, and according to a kinetics profile which can be adjusted by the composition of the di-block copolymers. Although complete release was not achieved, despite the high antibody-load (above 30%), a limited burst was observed, that was unexpected. All in all, as the filaments were loaded with a high amount of antibody, these filaments are promising for sustained delivery of antibody over time in patients in need of treatment.

It is the first time that low molecular weight amphiphilic di-block copolymers made of either PEG-PLA or PEG-PLGA sequences are used as pharmaceutical excipients to protect therapeutic proteins during drying procedures, such as spray-drying or freeze-drying. It was surprisingly found that they can replace all traditional low molecular weight excipients, while increasing the therapeutic proteins loading, better controlling their release rate, and avoiding their thermal denaturation during the preparation of a solid dosage form. The results reported above highlight the potency of low molecular weight amphiphilic di-block copolymers for drying and HME processing, but their effectiveness could also be considered for other methodologies where excipients are needed to stabilize and control the dissolution rate of biopharmaceutical drugs.

Most specifically it is worth to mention that according to the results reported above the most efficient low molecular weight amphiphilic di-block copolymer to stabilize an antibody during the drying step should have a well-balanced HLB with a similar Mw of the hydrophilic and lipophilic segments and a mean Mw close to 5000 Da. In contrast to usual large amount of low molecular weight excipient used to stabilize proteins or/and antibody during drying (i.e., 30%), the optimal content of the low molecular weight di-block copolymer can be limited to a maximal amount of 5 wt %.

In regard to the ability of these low molecular weight di-block copolymers to improve the interaction of an antibody and a polyester matrix during HME processing to achieve a sustained release formulation, the most attractive compositions of the low molecular weight di-block copolymer consist of 5 kDa-5 kDa or 5 kDa-2.5 kDa for PEG-P(d,l)LA sequences. Thanks to effectiveness to facilitate a homogeneous mixing of the protein within the polyester matrix, small % of these low molecular weight di-block are required (typically 1.5 wt %) to in the final HME formulations.

Surprisingly, adopting the optimal composition, macromolecular architecture and molecular weight, these low molecular di-block copolymers are able to assume the various functionalities requested to stabilize antibody during drying, including surface activity, water replacer, bulking and cohesiveness enhancer to the final solid. Being made from suitable and well equilibrated amphiphilic sequences these di-block or multi-block copolymers are also able to promote the intimate mixing of protein drugs within hydrophobic aliphatic polyester, while acting as plasticizer to reduce the temperature of processing, a critical aspect to avoid thermal degradation of biopharmaceutical drugs.

REFERENCES

1. Goyanes et al. (2015), Mol. Pharmaceutics 2015, 12:4077-4084
2. Tiwari et al. (2016) Expert Opinion On Drug Delivery, 13 (3): 451-464
3. Fredenberg et al. (2011), International Journal of Pharmaceutics, 415:34-52
4. Cossé et al. (2016), AAPS PharmSciTech., 18:15-26
5. Duque et al. (2018), International Journal of Pharmaceutics, 538:139-146
6. Ghalanbor et al. (2010), Pharmaceutical Research, 27 (2): 371-379
7. Mensink et al. (2017), European Journal of Pharmaceutics and Biopharmaceutics, 114:288-295
8. Emami et al. (2018) Pharmaceutics, 10, 131
9. Crowley et al. (2007), Drug Development and Industrial Pharmacy, 33:909-926 WO2015/197772
10. Sadia et al. (2016), International Journal of Pharmaceutics, 513 (1-2): 659-668
11. Regibeau, J. Hurlet, R. G. Tilkin, F. Lombart, B. Heinrichs and Ch. Grandfils, Synthesis of medical grade PLLA, PDLLA, and PLGA by a reactive extrusion, Polymerization, Materials Today Communications, 2020, 24, 101208, doi.org/10.1016/j.mtcomm.2020.101208

The invention claimed is:

1. A pharmaceutical composition comprising at least one stabilizer, an active ingredient, and optionally a buffering agent, a surfactant and/or at least one further stabilizer, wherein said active ingredient is a therapeutic protein and wherein said at least one stabilizer is a di-block or multi-block copolymer formed from the combination of at least one PEG and at least one polymer based on or selected from polyurethane (TPU), polyvinylpyrrolidone (PVP), polyvinyl alcohol (PVA), poly (ε-caprolactone) (PCL), poly(lactic acid) (PLA), polydioxanone, polyglycolide, polytrimethylene carbonate, hydroxypropyl cellulose (HPC), Hydroxypropyl methylcellulose (HPMC), any variants thereof or combinations thereof, wherein said therapeutic protein and said at least one stabilizer are present in a ratio of 100:1 to 6:1 (w/w).

2. The pharmaceutical composition according to claim 1, wherein the di-block or multi-block copolymer is selected from the group consisting of poly (lactide) poly (ethylene glycol) (PLA-PEG), poly (lactide) poly (ethylene glycol) poly (lactide) (PLA-PEG-PLA), poly (lactic-co-glycolic acid)-poly (ethylene glycol) (PLGA-PEG) poly[(lactide-co-ethylene glycol)-co-ethyloxyphosphate] (Poly (LAEG-EOP)) and Polyvinyl caprolactam-polyvinyl acetate-polyethylene glycol (PCL-PVA-PEG).

3. A filament comprising a freeze dried or spray dried pharmaceutical composition according to claim 1, a plasticizer, and a polymeric material.

4. The filament according to claim 3, wherein the polymeric material is poly(lactic-co-glycolic acid) (PLGA), poly (ε-caprolactone) (PCL), poly (lactic acid) (PLA), or combinations thereof.

5. The filament according to claim 3, wherein the plasticizer is polyethyleneglycol.

6. The filament according to claim 3, wherein the polymer is in a range of about 50 to 75% (w/w) and wherein the plasticizer is in a range of about 2 to 20% (w/w).

7. The filament according to claim 3, wherein the plasticizer and the polymeric material are replaced in all or in part by a di-block copolymer or multi-block copolymer formed from the combination of at least one PEG and at least one polymer based on polyurethane (TPU), polyvinylpyrrolidone (PVP), polyvinyl alcohol (PVA), poly (ε-caprolactone) (PCL), poly(lactic acid) (PLA), polydioxanone, polyglycolide, polytrimethylene carbonate, hydroxypropyl cellulose (HPC), Hydroxypropyl methylcellulose (HPMC), any variants thereof or combinations thereof.

8. The filament according to claim 7, wherein the di-block or multi-block copolymer is selected from the group consisting of poly (lactide) poly (ethylene glycol) (PLA-PEG), poly (lactide) poly (ethylene glycol) poly (lactide)(PLA-PEG-PLA), poly(lactic-co-glycolic acid)-poly (ethylene glycol) (PLGA-PEG) poly[(lactide-co-ethylene glycol)-co-ethyloxyphosphate] (Poly (LAEG-EOP)), and Polyvinyl caprolactam-polyvinyl acetate-polyethylene glycol (PCL-PVA-PEG).

9. The filament according to claim 7, wherein the di-block copolymer or multi-block copolymer is in a total amount within the range of about 55 to 85% (w/w).

10. The filament according to claim 3, wherein the active ingredient is homogeneously dispersed into the at least one stabilizer or into the polymeric matrix.

11. The filament according to claim 3, wherein the therapeutic protein is a cytokine, a growth factor, a hormone, an antibody or a fusion protein.

12. The filament according to claim 3, wherein the active ingredient loading is in the range of 5 to 40% (w/w).

13. The filament according to claim 3, wherein the ratio protein: stabilizer is between 1:1 and 5:1 (w/w).

14. An implantable drug delivery device comprising the filament according to claim 3.

15. The implantable drug delivery device according to claim 14, wherein the device comprises at least one internal hollow cavity.

16. The implantable drug delivery device according to claim 14, wherein the device is a fully solid object.

17. A 3D printed implantable drug delivery device obtained by 3D printing the filament according to claim 3.

18. A process for producing a filament, the process comprising the steps of:

a) preparing a liquid pharmaceutical composition according to claim 1, b) freeze-drying or spray-drying the liquid pharmaceutical composition of step a) to obtain a powder, c) dispersing homogeneously the powders of step b) with a plasticizer and at least one polymeric material, and d) spinning or extruding the dispersion of step c) to obtain a filament.

19. The pharmaceutical composition according to claim 1, wherein the composition further comprises at least one further stabilizer, a buffering agent, and/or surfactant.

20. The pharmaceutical composition according to claim 1, wherein said therapeutic protein and said at least one stabilizer are present in a ratio of 20:1 to 10:1 (w/w).

* * * * *